(12) United States Patent  
Lee et al.

(10) Patent No.: US 9,199,216 B2  
(45) Date of Patent: Dec. 1, 2015

(54) APPARATUSES AND METHODS FOR CONDITIONING AND REORIENTING COMPONENTS OF AN ELECTROPHYSIOLOGY MEASUREMENT SYSTEM

(75) Inventors: Lawrence Lee, Sunnyvale, CA (US); Windsor Owens, San Francisco, CA (US)

(73) Assignee: Molecular Devices, LLC, Sunnyvale, CA (US)

( * ) Notice: Subject to any disclaimer, the term of this patent is extended or adjusted under 35 U.S.C. 154(b) by 614 days.

(21) Appl. No.: 13/569,137

(22) Filed: Aug. 7, 2012

(65) Prior Publication Data

US 2014/0042039 A1 Feb. 13, 2014

(51) Int. Cl.
*G01N 27/28* (2006.01)
*B01J 19/08* (2006.01)
*G01N 33/487* (2006.01)

(52) U.S. Cl.
CPC ........... *B01J 19/08* (2013.01); *G01N 33/48728* (2013.01)

(58) Field of Classification Search
CPC . G01N 27/28; G01N 33/48728; G01N 27/38; G01N 27/27; B01J 19/08; B01J 19/126; B01J 19/123; B25J 9/02; B25J 9/04; B25J 9/042; B25J 9/106; C12Q 1/005; C12Q 1/006
See application file for complete search history.

(56) References Cited

U.S. PATENT DOCUMENTS

| | | | |
|---|---|---|---|
| 7,270,730 B2 | 9/2007 | Schroeder et al. | |
| 7,322,926 B2 | 1/2008 | Due et al. | |
| 8,048,289 B2 | 11/2011 | Finkel | |
| 2005/0111956 A1* | 5/2005 | van der Meulen | 414/744.2 |

OTHER PUBLICATIONS

IonWorks Barracuda Automated Patch Clamp System User Guide, Feb. 2012, pp. 1-45.
Utility U.S. Appl. No. 13/569,119, filed Aug. 7, 2012, entitled: "Centrifuge Apparatus, Centrifuge Tubes, and Methods for Automated Cell Preparation".
Utility U.S. Appl. No. 13/569,129, filed Aug. 7, 2012, entitled: "Apparatus and Method for Separating Materials of Different Densities".

* cited by examiner

*Primary Examiner* — Xiuyu Tai
(74) *Attorney, Agent, or Firm* — Bella Fishman

(57) ABSTRACT

An apparatus for automatically conditioning a patch plate and a plenum of an electrophysiology measurement system is provided. An arm is linearly movable between a non-operative position and an operative position. An end effector mounted to one side of the arm is configured to condition the patch plate. Another end effector mounted to an opposite side of the arm is configured to condition the plenum. A linear actuator is coupled to the arm and is configured to drive movement of the arm between the operative position and the non-operative position. When the arm is positioned in the operative position, the arm is situated between the patch plate and the plenum.

6 Claims, 21 Drawing Sheets

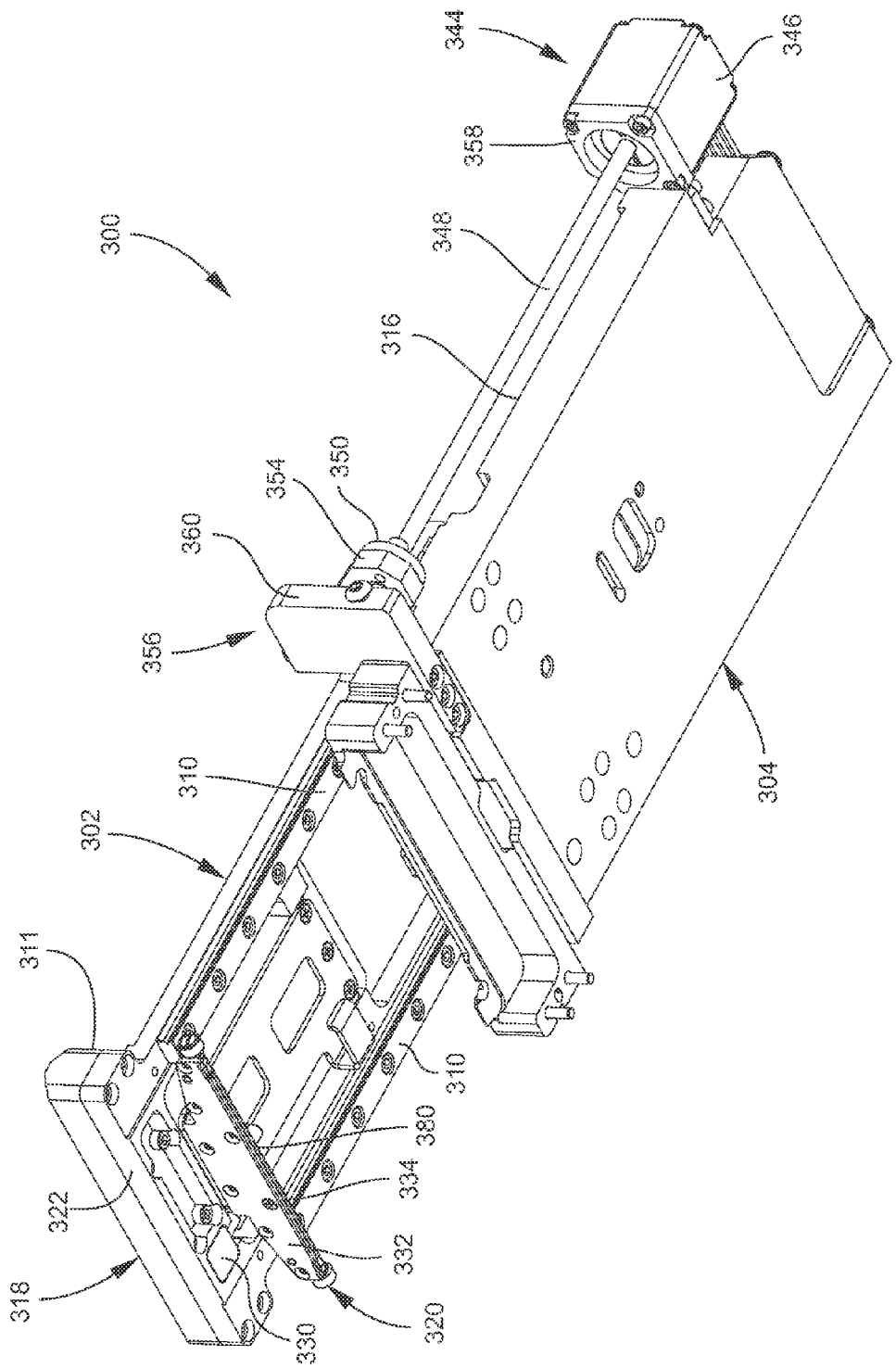

APPARATUSES AND METHODS FOR CONDITIONING AND REORIENTING COMPONENTS OF AN ELECTROPHYSIOLOGY MEASUREMENT SYSTEM

RELATED APPLICATIONS

This application is related to utility patent applications titled CENTRIFUGE APPARATUS, CENTRIFUGE TUBES, AND METHODS FOR AUTOMATED CELL PREPARATION and APPARATUS AND METHOD FOR SEPARATING MATERIALS OF DIFFERENT DENSITIES both filed on Aug. 7, 2012.

TECHNICAL FIELD

This invention relates to electrophysiology and systems and apparatus utilized to carry out electrophysiology-related measurements and assays, particularly in an automated and semi-automated manner. More specifically, the invention relates to apparatus and methods for conditioning or handling components of such systems.

BACKGROUND

The electrical behavior of cells and cell membranes is of profound importance in basic research as well as in modern drug development. A specific area of interest in this field is in the study of ion channels and transporters. Ion channels are protein-based pores found in the cell membrane that are responsible for maintaining the electrochemical gradients between the extracellular environment and the cell cytoplasm. Ion channels are passive elements in that, once opened, ions flow in the direction of existing electrochemical gradients.

The study of ion channels is a very diverse and prolific area encompassing basic academic research as well as biotechnical and pharmaceutical research. Electrophysiology is performed on isolated cell membranes or vesicles as well as on synthetic membranes where solubilized channels are reconstituted into a manufactured membrane. Instrumentation for automated, high-throughput studies of ion channels have been developed and may be referred to as high-throughput electrophysiological measurement systems.

Automated high-throughput electrophysiology measurement systems may employ patch plates clamped to a plenum. The space between the patch plate and the plenum may be filled with an electrically conductive buffer solution to form an electrical connection between electrodes in the plenum and target cells contained in the patch plate. The electrodes may thus measure electrical properties of target cells during assays.

At the conclusion of the assay, a robotic plate handler may transfer the patch plate to other locations at the system. Residual buffer solution on the bottom of the patch plate, however, may drip onto sensitive components of the system as the robotic plate handler transfers the patch plate between locations, which can damage those components or create contamination issues. Additionally, buffer solution that remains in the plenum may entrap bubbles when the plenum is subsequently refilled. Bubbles entrapped in the plenum may cause a lack of electrical continuity between electrodes, which can result in failures during electrophysiology testing. Moreover, electrodes of the system may degrade over time due to chemical and electrical activity at the electrodes. As a result, the electrodes may need to be periodically reconditioned between assays. Therefore, there is a need for conditioning the patch plate, plenum, and other components of an automated high-throughput electrophysiology measurement system.

Automated high-throughput electrophysiology measurement systems may include robotic plate handlers to manipulate microtitre plates ("microplates") and other transportable components (e.g., pipette tip boxes) during assays. Successful automation of assays depends on the ability of the robotic plate handler to accurately load and place the microplates (or other components) into various devices or locations of the system, which may involve accurately positioning and orienting the microplates often to within precise tolerances.

As the robotic plate handler moves the microplates between devices, slight positioning offsets and orientation offsets may occur and accumulate. Position offsets and orientation offsets can result in position and orientation errors when attempting to load and place the microplates. To avoid position errors and orientation errors, devices to reposition and reorient the microplates may be employed. Conventional devices may include passive features to reposition and reorient the microplates. These conventional devices, however, may not be equipped to overcome the dimensional tolerances of standard microplates, which can vary in length and width by up to, for example, 1 millimeter (mm) or more.

Furthermore, microplates may need to be repositioned or reoriented in some situations in order to align the microplates with devices oriented at incompatible angles. Moreover, microplates may include a bar code applied to one side, and because there is no standardized position for the bar code, microplates may need to be reoriented in order to bring the bar code within view of a bar code reader. Therefore, a need also exists for apparatuses and methods to automatically reposition and reorient microplates and other similarly-sized components.

SUMMARY

An apparatus for automatically conditioning a patch plate and a plenum of an electrophysiology measurement system is provided. An arm is linearly movable between a non-operative position and an operative position. An end effector mounted to one side of the arm is configured to condition the patch plate. Another end effector mounted to an opposite side of the arm is configured to condition the plenum. A linear actuator is coupled to the arm and is configured to drive movement of the arm between the operative position and the non-operative position. When the arm is positioned in the operative position, the arm is situated between the patch plate and the plenum.

A method for automatically condition a patch plate and a plenum of an electrophysiology measurement system is also provided. An arm is moved from a non-operative position to an operative position between the patch plate and the plenum. At least one end effector mounted to the arm. One end effector mounted one side of the arm conditions the patch plate. Another end effector mounted to an opposite side of the arm conditions the plenum.

An apparatus for automatically reorienting a patch plate of an electrophysiology measurement system is additionally provided. A linearly moveable platform is configured to support the Patch plate. The platform includes a cornering arm configured to pivot into contact with the patch plate. A frame has an opening sized and shaped to permit movement of the platform through the opening. An elevating arm is mounted to the platform and is configured to move the platform through the opening. A linear actuator is mounted to the elevating arm and is configured to drive movement of the elevating arm. One or more cornering cams are mounted near one or more respective interior edges of the opening. The cornering cams are configured to engage the cornering arm such that the cornering arm pivots toward the platform and pushes the patch plate into a reference corner of the platform.

A method for automatically reorienting a patch plate of an electrophysiology measurement system is further provided. A platform having a pivotable cornering arm is lowered into an opening of a frame. When the platform is positioned within the opening, a cam-engagement end of the cornering arm is pivoted toward the platform, and a plate-engagement end of the cornering arm is pivoted away from the platform. The patch plate is deposited on the platform, and the platform is raised out of the opening such that the cam-engagement end of the cornering arm pivots away from the platform, and the plate-engagement end of the cornering arm pivots toward the platform and pushes the patch plate into a reference corner of the platform.

BRIEF DESCRIPTION OF THE DRAWINGS

The invention may be better understood by referring to the following figures. The components in the figures are not necessarily to scale, emphasis instead being placed upon illustrating the principles of the invention. In the figures, like reference numerals designate corresponding parts throughout different views.

FIG. 7B is a rear bottom-left perspective view of the automated conditioning apparatus of FIG. 5 shown in an assembled configuration.

DETAILED DESCRIPTION

An automated conditioning apparatus may be provided as part of a process deck of an automated high-throughput electrophysiology measurement system. The automated conditioning apparatus may operate to condition the plenum of an analysis station and a patch plate at the analysis station. Conditioning the patch plate and plenum may involve aspirating residual fluid from these components in order to dry the components between assays, and/or other types of conditioning as described by example below. An automated reorientation apparatus may also be provided at the process deck or adjacent to the process deck such as at a landing pad. The automated reorientation apparatus may operate to reorient (e.g., rotate and/or readjust the position of) a patch plate or other similarly sized component. These and other aspects relating to the apparatuses and associated methods and systems will be discussed in further detail below by way of examples.

Figure 1:
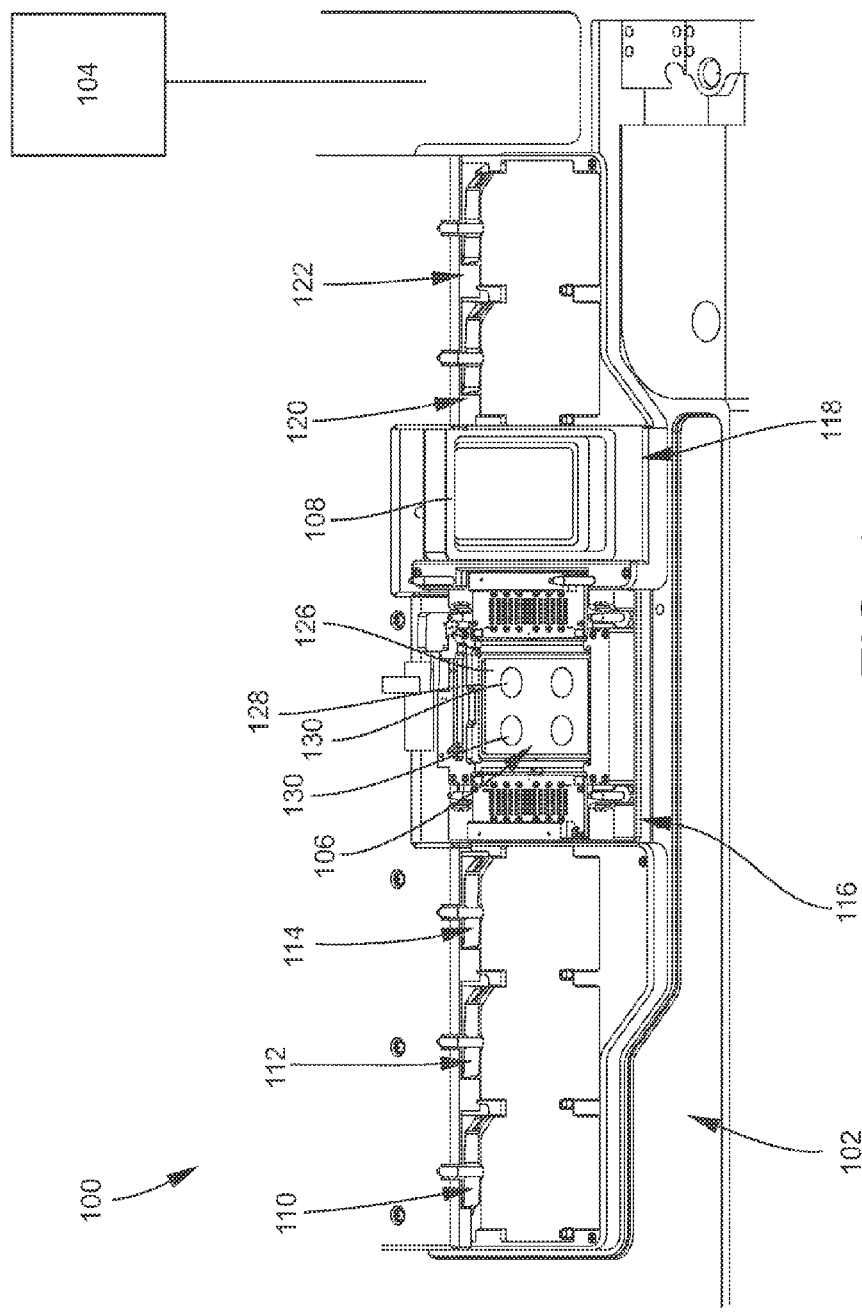
FIG. 1 is a top view of an example of an implementation of an automated high-throughput electrophysiology measurement system.

Referring to FIG. 1, an example of an implementation of an automated high-throughput electrophysiological measurement system 100 is shown in a top view. The system 100, in this example, is configured to conduct simultaneous measurements on multiple samples (e.g., a two-dimensional grid or array of samples). The high-throughput electrophysiological measurement system 100 may include a measurement platform 102, which may also be referred to as a process deck 102. The process deck 102 may support the various components of the system 100 and may comprise a generally planar surface for supporting or maintaining a desired spatial arrangement of some or all of the components of the measurement system 100.

The system may include a control module 104 that controls operation of the system 100 during an assay. The control module 104 may include, for example, an external microcomputer, display device, and software user interface. The control module 104 may also include a microcontroller interfaced to the external microcomputer for controlling the real-time functional aspects of the system 100 including motion control, fluidics control, and electrical data recording.

The system 100 may also include a patch engine that controls the components of the system 100, performs electrophysiological measurements, and digitizes the data acquired during patch clamp assays. The patch engine, in this example, includes a plenum 106, electrode plate 108, and data acquisition engine. These components will be discussed in further detail below.

The system 100 may include multiple stations or modules configured for implementing various functions. In the illustrated example, the system 100 includes seven stations: a tip rack station 110; an external buffer station 112; a first compound station 114; an analysis station 116; a wash station 118; a second compound station 120; and a cell station 122. It will be understood that the system 100 may include more or less stations, including stations providing functions different from those just noted.

Each of the stations, in this example, is shaped to receive an SBS-standard 384-well microtitre plate (Society for Biomolecular Sciences). In other words, the stations, in this example, may be described as having an SBS-standard 384-well microplate footprint. Assay steps take place at the process deck 102, and a robotic pipettor head delivers fluids from the external buffer station 112, cell station 122, and compound stations 114 and 120 to a measurement substrate at the analysis station 116. The robotic pipettor head will be discussed further below with reference to FIG. 2.

The measurement substrate may be referred to as the patch plate and may include multiple holes or apertures around which corresponding samples (e.g., cells or cell membranes) may be positioned or sealed for analysis. The patch plate, in this example, is an SBS-standard 384-well microplate. Accordingly, the patch plate, in this example, includes 384 individual wells for holding cells, external buffer solution, and biological screening compounds. The 384 wells of the patch plate, in this example, may be arranged in a grid of 16 rows (identified as A-P) and 24 columns (identified as 1-24). The wells of the patch plate may include one or more apertures formed through the lower surface. Each aperture may have a diameter of, for example, about 2 micrometers (μm). A patch plate having one aperture per well may be referred to as a single-hole plate. A patch plate having multiple apertures per well (e.g., an array of 64 apertures) may be referred to as a population patch clamp (PPC) plate. The patch plate may be moved to and from the analysis station during an assay. The patch plate will be discussed further below with reference to FIG. 3.

The tip rack station 110 holds a tray that may be preloaded with pipettor tips. The robotic pipettor head may lower onto the tip rack station 110 to load the pipettor tips at the start of an assay. The pipettor tips may be utilized to aspirate and dispense external buffer solution, compounds, and cells at appropriate times during a given assay, depending on the particular method specified for the assay.

The external buffer station 112 may also be referred to as an input station and may include an external buffer boat that holds external buffer solution. In some example implementations, a peristaltic pump and vacuum-assisted waste bottle may be selectively employed to automatically fill and drain the external buffer station 112. The external buffer boat may be filled with external buffer solution prior to the start of an assay. The external buffer solution may be a physiological saline solution comprising a salt or mixture of salts that mimics extracellular solution (e.g., a solution containing low concentrations of potassium). The robotic pipettor head may aspirate the external buffer solution from the external buffer station 112, transport the external buffer solution to the analysis station 116, and dispense the buffer solution into the wells of the patch plate.

The first and second compound stations 114 and 120 may also be referred to as input stations and hold biological screening compounds or other types of reagents that may be utilized during the assay. An SBS-standard 384-well compound plate (e.g., a microplate) may hold the biological screening compounds and reside within the footprint at the first or second compound station 114 or 120. The robotic pipettor head may similarly aspirate the compounds from the compound stations 114 and 120, transport the compounds to the analysis station 116, and dispense the compounds into the wells of the patch plate.

The analysis station 116 includes the plenum 106 of the patch engine and supports the patch plate during the assay. The plenum 106 includes a reservoir 126, and an internal buffer solution may be pumped into and out of the plenum reservoir 126 from below during an assay. The internal buffer solution may be a saline solution comprising a salt or mixture of salts that mimics the internal cytoplasm of a living cell (e.g., a solution containing high concentrations of potassium). The patch plate rests on the plenum 106, and an o-ring 128 surrounding the perimeter of the plenum 106 creates an air-tight seal between the patch plate and the plenum reservoir 126. A small negative (differential) pressure is introduced that pulls cells (or cell membranes) residing in the wells toward the aperture at the bottom of the well. The differential pressure thus forms a high-resistance electrical seal between the cell (or cell membrane) and the bottom of the well, as appreciated by persons skilled in the art.

The electrode plate 108 may be referred to as an electronics head and used to perform electrophysiological measurements on cell samples at the patch plate. Electrophysiological measurements may be performed by forming an electrical circuit across the apertures in the wells of the patch plate. An electrical circuit may be formed by positioning electrodes on opposite sides of the membrane of the patch plate. For example, a sense electrode may be positioned above the membrane, and a ground electrode may be positioned below the membrane. Accordingly, the plenum 106, in this example, includes four ground electrodes 130 positioned at the top of the plenum reservoir 126, and the electrode plate 108, in this example, may include an array of sense electrodes 132 housed in a frame that fits on top of the patch plate and plenum. The electrode plate 108 will be discussed in further detail below with reference to FIG. 2 and FIG. 3.

The arrangement of the sense electrodes 132 of the electrode plate 108 may correspond to the arrangement of the wells of the patch plate such that each sense electrode 132 may perform an electrophysiological measurement at a respective well of the patch plate. Accordingly, the electrode plate 108, in this example, may include an array of 384 sense electrodes 132. Each sense electrode 132 may correspond to an electronic channel. Accordingly, the 384 sense electrodes 132 in this example correspond to 384 electronic channels.

The electrodes 132 may be, for example, silver or silver-coated pins (i.e., Ag/AgCl). To complete the circuit, a suitable electrolyte (e.g., saline) solution may be added to the wells of the patch plate and the plenum reservoir 126. For example, the external buffer solution and the internal buffer solution may contain chloride ions to enable the sense electrodes 132 and ground electrodes 130 to monitor electrical activity.

The electrode plate 108 may be clamped to the plenum 106 during an assay such that the sense electrodes 132 are received into respective wells of the patch plate. The electrode plate 108 may include apertures formed through its upper surface to provide access to the pipettor tips. In this way, the electrode plate 108 allows for the addition of compounds to the patch plate wells while simultaneously measuring ion current in the wells. As discussed further below with reference to FIG. 3, the sense electrodes 132 and the ground electrodes 130 may be coupled to measurement electronics to obtain data relating to the electrophysiological measurements.

The wash station 118 may receive various components in order to clean those components following an assay. The wash station 118, in this example, includes a reservoir that accommodates the pipettor tips and the electrode pins of the electrode plates for the washing procedures. Accordingly, the wash station 118, in this example, may include a manifold of input ports that match the dimensionality of the pipettor tips and electrode pins. A fluid handling system (not shown) may pump cleaning solution through the wash station 118, which may then empty into waste carboys (not shown) below the process deck 102. The wash station 118 may also serve as a resting position for the electrode plate when not in use. The robotic pipettor head may pick up the electrode plate 108 at the wash station 118 and transport the electrode plate 108 to the analysis station 116 during an assay. The robotic pipettor head may then return the electrode plate 108 to its resting position at the wash station 118 at the conclusion of an assay.

The cell station 122 may also be referred to as an input station and include a cell boat that holds the cells (or other biological samples) used in an assay. The cells may be suspended in an external buffer solution while residing in the cell boat. The robotic pipettor head may similarly aspirate the cells from the cell station 122, transport the cells to the analysis station 116, and dispense the cells into the wells of the patch plate.

Figure 2:
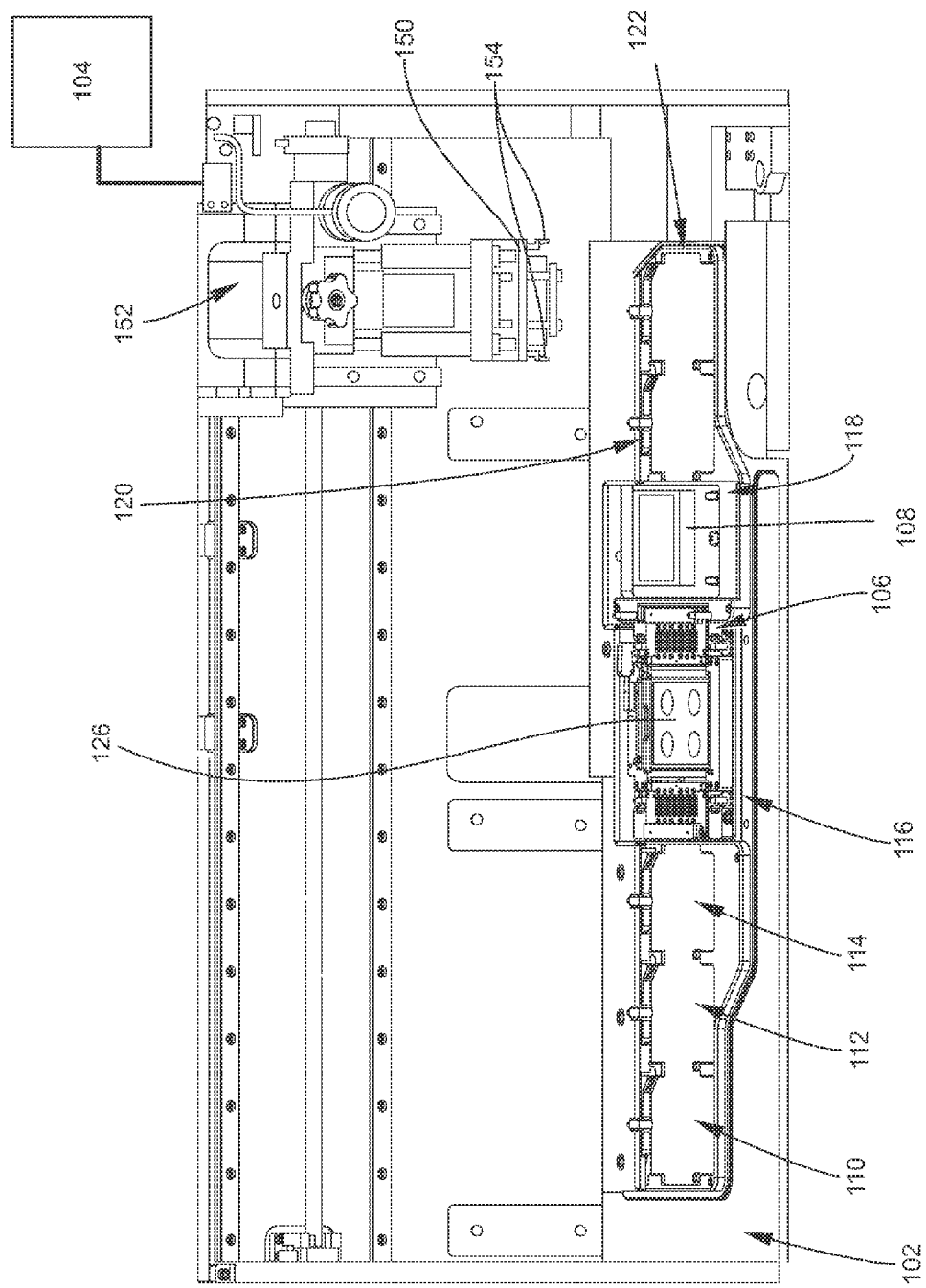
FIG. 2 is a side view of an example of an implementation of a robotic pipettor head of an automated high-throughput electrophysiology measurement system.

Referring now to FIG. 2, an example of an implementation of a robotic pipettor head 150 for a high-throughput electrophysiology measurement system 100 is shown in a side view. The robotic pipettor head 150 may also be referred to as a fluidics head or a multi-channel dispensing head. The robotic pipettor head 150 may be used to add, remove, replace, or transfer fluids, cell solutions, and compounds into the wells of a patch plate. The robotic pipettor head 150, in this example, may hold the pipettor tips utilized to transport fluids from the cell station 122, the external buffer station 112, and the compound stations 114 and 120 to the analysis station 116. The pipettor tips aspirate or dispense the fluids in precise amounts according to the assay protocols.

The robotic pipettor head 150 may be coupled to a three-dimensional mechanical gantry system 152 for moving the robotic pipettor head 150 between the stations of the process deck. The control module 104 may communicate with the mechanical gantry system 152 to control the movement of the robotic pipettor head 150 during an assay.

At the start of an assay, the robotic pipettor head 150 may move to the tip rack station 110 and load the pipettor tips. The robotic pipettor head 150 may also serve as the transport mechanism for the electrode plate 108. Accordingly, the robotic pipettor head 150 may, for example, include electrode plate transport clips 154 that hold the electrode plate 108. The robotic pipettor head 150 may load the electrode plate 108 from its resting position at the wash station 118 and transport it to the analysis station 116 where it clamps to the plenum 106 during the assay. At the conclusion of the assay, the robotic pipettor head 150 may load the electrode plate 108 from the analysis station 116 and transport it back to the wash station 118.

Figure 3:
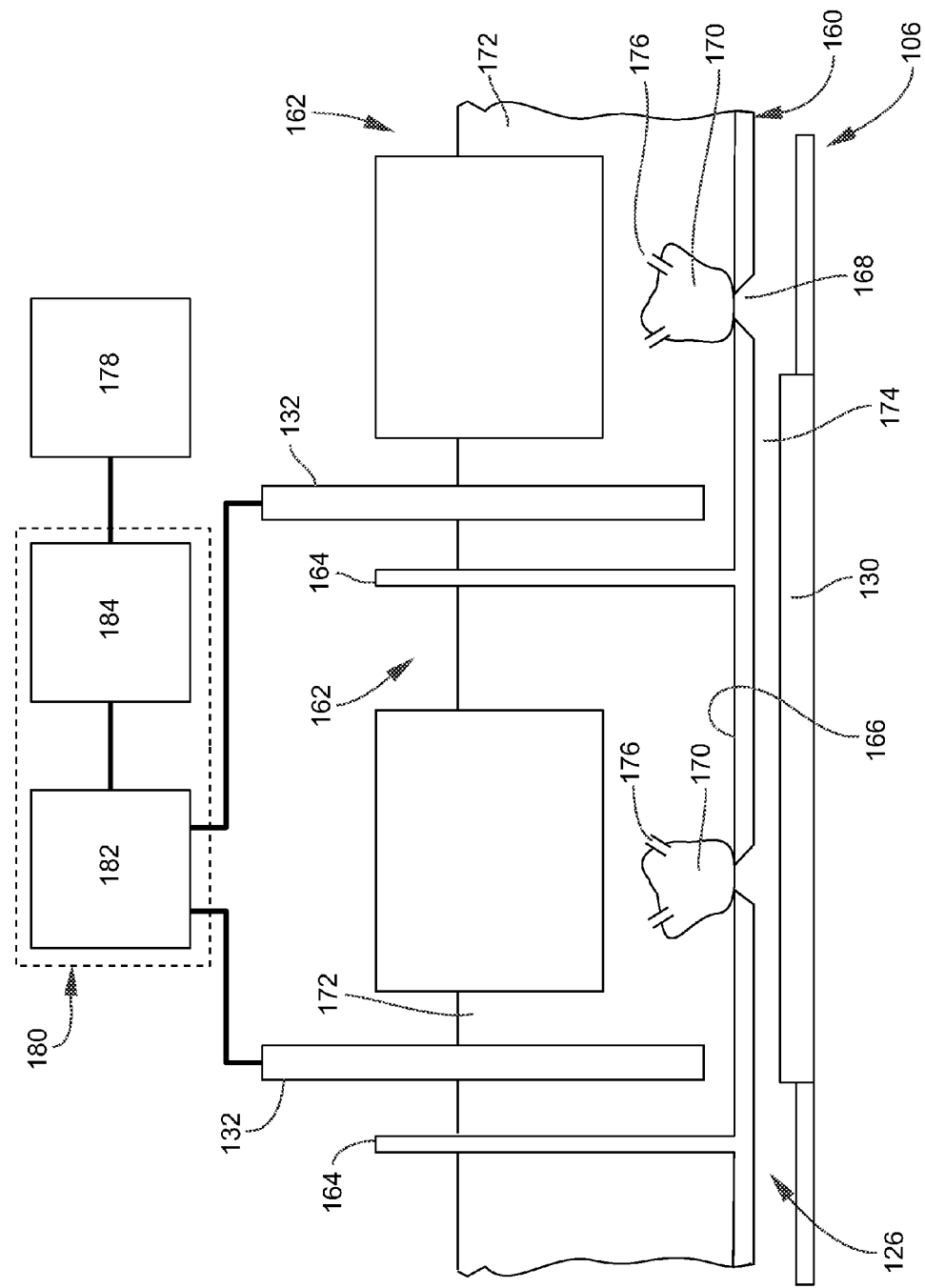
FIG. 3 is a side cross-sectional view of an example implementation of a patch plate supported on a plenum of an automated high-throughput electrophysiology measurement system.

Referring now to FIG. 3, an example implementation of a patch plate 160 supported by a plenum 106 of a high-throughput electrophysiology measurement system 100 is shown. The patch plate 160 may include multiple wells 162 as discussed above (e.g., 384 wells). Two wells 162 of the patch plate 160 are shown by way of example in FIG. 3. Each well 162 is partitioned by a well wall 164 and bounded by the bottom 166 of the patch plate 160. Additionally, the wells 162 in the example patch plate 160 of FIG. 3 each include an aperture 168 formed through the bottom 166 of the patch plate 160. Cells 170 in the respective wells 162 may be sealed to the bottom 166 of the patch plate 160 via differential pressure as discussed above.

The wells 162 of the patch plate 160 may be filled with external buffer solution 172, and the plenum reservoir 126 of the plenum 106 situated beneath the patch plate 160 may be filled with internal buffer solution 174. Sense electrodes 132 may be positioned in the respective wells 162 of the patch plate 160 to measure the electrical activity occurring in the wells 162 during the assay, such as the activity of ion channels 176 of the cells 170 as appreciated by persons skilled in the art. The ground electrodes 130 of the plenum 106 may complete the electrical circuits across the respective apertures 138 of the patch plate 160.

The sense electrodes 132 of the electrode plate 108 and the ground electrodes 130 may communicate with the data acquisition engine 178 via measurement electronics 180 such as, for example, a programmable voltage source (not shown), an amplifier 182 and analog-to-digital converter (ADC) 184. As seen in the example shown in FIG. 3, the sense electrodes 132 and the ground electrodes 130 are in signal communication with the amplifier 182, which is in signal communication with the ADC 184, which is in turn in signal communication with the data acquisition engine 178. The amplifier 182 may be a high-gain, low-noise trans-impedance amplifier that converts the current measured on the sense electrode 132 to an analog voltage signal. The ADC 184 may convert the analog voltage signal from the amplifier 182 into a digital voltage measurement. The data acquisition engine 178 may thus save the digital voltage measurements for the sense electrode channels in a computer memory.

Figure 4:
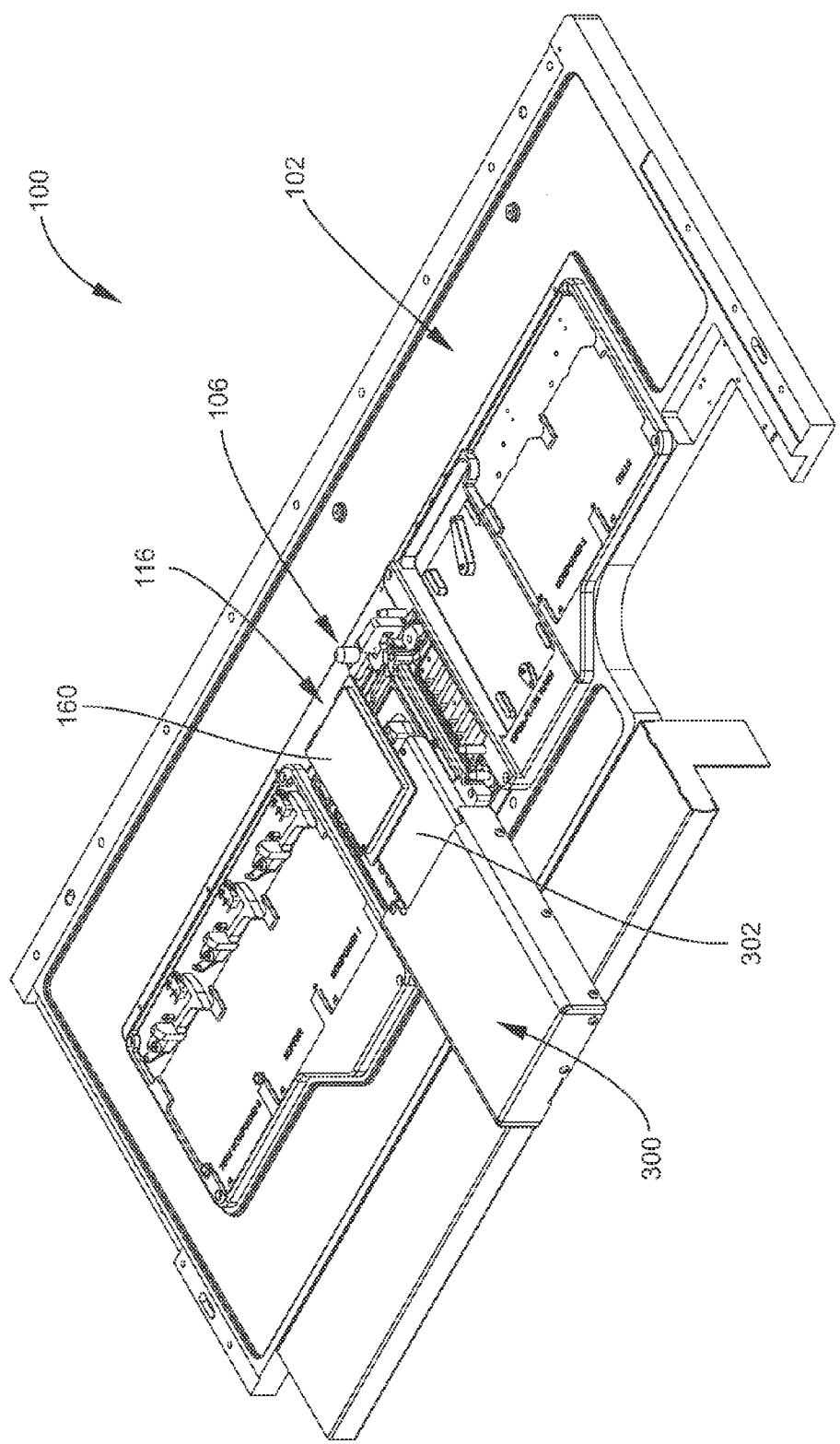
FIG. 4 is a front top-right perspective view of an example of an implementation of an automated conditioning apparatus installed at the process deck of an automated high-throughput electrophysiology measurement system.

Referring to FIG. 4, a front top-right perspective view of an example of an implementation of an automated conditioning apparatus 300 installed at the process deck 102 of an automated, high-throughput electrophysiology measurement system 100 is shown. The automated conditioning apparatus 300 is positioned near the analysis station 116 of the process deck 102 and includes a displaceable robotic conditioning arm 302 for conditioning a patch plate 160 and the plenum 106 at the process deck 102. The robotic conditioning arm 302 is displaceable between a non-operative position and an operative position. The robotic conditioning arm 302, in this example, moves linearly from the non-operative position to the operative position in order to position itself between the patch plate 160 and the plenum 106.

Figure 5:
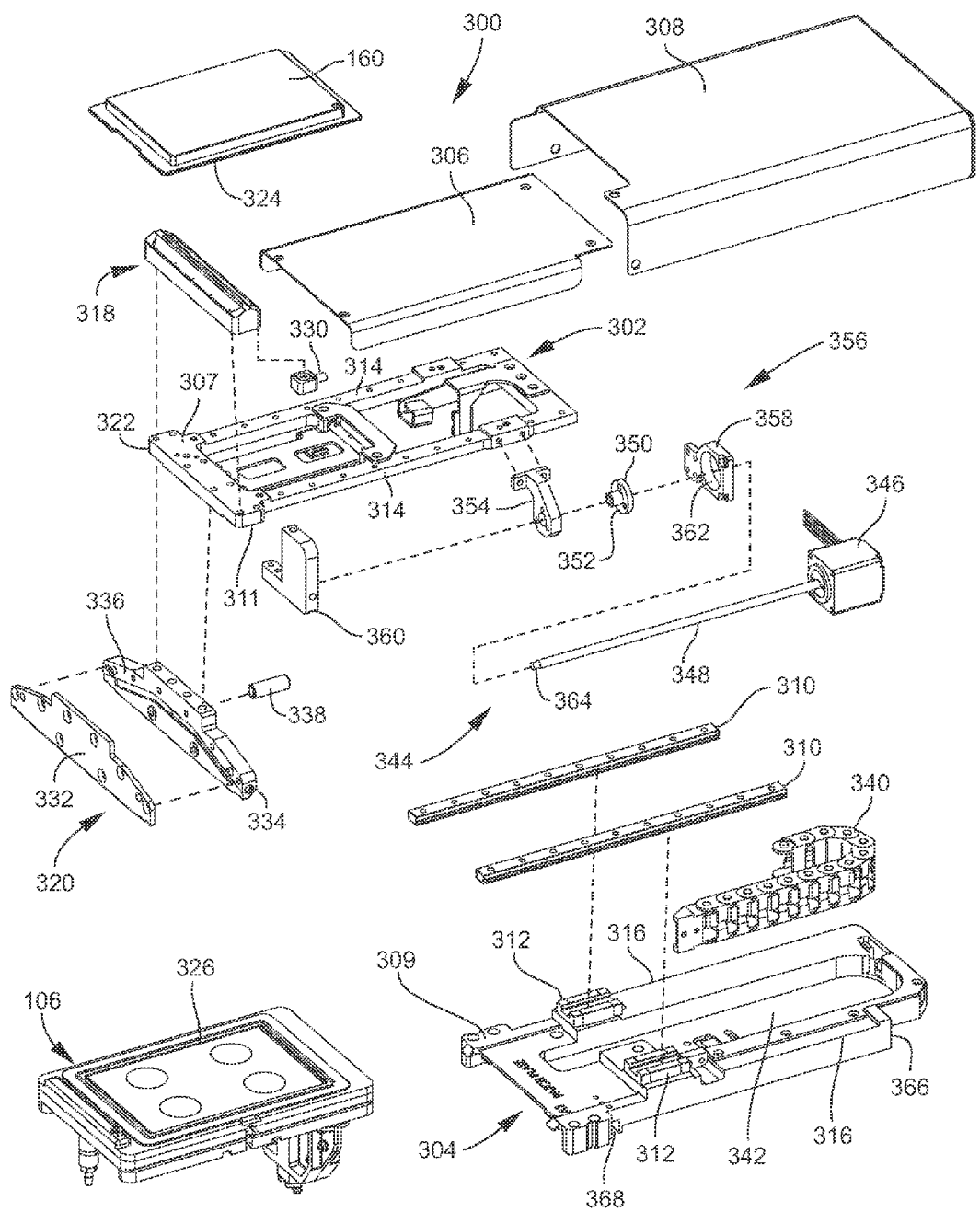
FIG. 5 is an exploded view of the automated conditioning apparatus of FIG. 4.

In FIG. 5, an exploded view of the automated conditioning apparatus 300 of FIG. 4 is shown. The automated conditioning apparatus 300, in this example, includes a mounting frame 304 and a robotic conditioning arm 302. The mounting frame 304 is secured to the process deck (102 in FIG. 4) of the automated, high-throughput electrophysiology measurement system (100 in FIG. 4)) next to a plenum 106 at an analysis station (116 in FIG. 4). The robotic conditioning arm 302, in this example, is a rigid frame having a substantially rectangular shape. The mounting frame 304, in this example, also has a substantially rectangular shape. A robotic arm cover 306 may be attached to the top side 307 of the robotic conditioning arm 302, and a mounting frame cover 308 may be attached to the top side 309 of the mounting frame 304 in order to protect the components of the automated conditioning apparatus 300.

The robotic conditioning arm 302 is mounted to the mounting frame 304 via a pair of guide rails 310 and guide blocks 312. The guide rails 310 are mounted to the underside of the robotic conditioning arm 302 with one guide rail 310 positioned along each longitudinal edge 314 of the robotic conditioning arm 302. The guide blocks 312 are mounted to the top side 309 of the mounting frame 304 at respective longitudinal edges 316 of the mounting frame 304. The guide blocks 312, in this example, receive the guide rails 310 in a tongue-and-groove fashion. In this way, the robotic conditioning arm 302 may slide across the mounting frame 304 from the non-operative position to the operative position between the patch plate 160 and plenum 106.

The robotic conditioning arm 302, may include one or more end effectors. In the illustrated example, the robotic conditioning arm 302 includes a pair of end effectors 318 and 320 mounted to an operative end 322 of the arm 302. One of the end effectors 318, in this example, is mounted to the top side 307 of the robotic conditioning arm 302 and may be referred to as an upper end effector. The other end effector 320, in this example, is mounted to the bottom side 311 of the robotic conditioning arm 302 and may be referred to as a lower end effector. The operative end 322 of the robotic conditioning arm 302, in this example, is the end of the robotic conditioning arm 302 that extends to the operative position between the patch plate 160 and the plenum 106.

As seen in FIG. 5, the upper end effector 318 faces upward to condition the underside 324 of the patch plate 160 (i.e., the bottom surface of the patch plate) and the lower end effector 320 faces downward to condition the top side 326 of the plenum 106 (i.e., the top surface of the plenum). As an example, conditioning the patch plate 160 and plenum 106 may include aspirating residual fluid from the patch plate 160 and the plenum 106 in order to dry these components between assays. In this example, the end effectors 318 and 320 may include vacuum nozzles and be configured to aspirate the residual fluid from the patch plate 160 and plenum 106. In this regard, the upper end effector 318 may also be referred to as the patch plate nozzle, and the lower end effector 320 may be referred to as the plenum nozzle.

The patch plate nozzle 318 includes an input aperture 328 formed along the top side of the nozzle 318 through which the residual fluid is received when aspirated from the underside 324 of the patch plate 160. The patch plate nozzle 318 also includes an internal channel (not shown) that fluidly interconnects the input aperture 328 to an output aperture (not shown) formed at the underside of the nozzle 318. The input aperture 328, internal channel, and output aperture may thus define a flow path far the residual fluid to travel along when aspirated from the underside 324 of the patch plate 160. A conduit fitting 330 may be connected to the output aperture for connecting a conduit line (FIG. 6) to the patch plate nozzle 318. As discussed further below, the conduit line may transport the aspirated fluid away from the patch plate nozzle 318.

The plenum nozzle 320 may aspirate residual fluid from the top side 326 of the plenum 106 in a similar fashion. The plenum nozzle 320, in this example, includes a faceplate 332 and nozzle body 334. When the faceplate 332 is attached to the nozzle body 334, the faceplate 332 and nozzle body 334 define an input aperture (FIG. 7B) on the underside of the plenum nozzle 320 through which the residual fluid is received when aspirated from the top side 326 of the plenum 106. Like the patch plate nozzle 318, the plenum nozzle 320 includes an internal channel 336 that fluidly interconnects the input aperture to an output aperture (not shown) formed in the back side of the nozzle body 334. The input aperture, internal channel 336, and output aperture may thus similarly define a flow path for the residual fluid to travel along when aspirated from the plenum 106. A conduit fitting 338 may likewise be connected to the output aperture for connecting a conduit line (FIG. 6) to the plenum nozzle 320.

Conduit lines (372 in FIG. 6) connected to the conduit fittings 330 and 338 of the nozzles 318 and 320 may reside within an energy chain 340 that resides within a recess 342 formed in the top side 309 of the mounting frame 304. In this way, the energy chain 340 may guide movement of the conduit lines across the mounting frame 304 as the robotic conditioning arm 302 moves from the non-operative position to the operative position.

The automated conditioning apparatus 300 may also include a linear actuator 344 that drives the robotic conditioning arm 302 from the non-operative position to the operative position between the patch plate 160 and plenum 106. The linear actuator 344, in this example, includes a motor 346 connected to a lead screw 348 that engages a lead nut 350. A flange 352 on the lead nut 350 may be used to mount the lead nut 350 to a lead arm 354. As shown by way of example, in FIG. 5, the lead arm 354 is mounted to one of the longitudinal edges 314 of the robotic conditioning arm 302.

The motor 346 may be a stepper motor (e.g., a Nema 11 stepper motor) and rotate the lead screw 348. The lead screw 348, in this example, includes threads that engage threads on the inner surface of the lead nut 350. Because the lead nut 350 is mounted to the lead arm 354 and the lead arm 354 is mounted to the robotic conditioning arm 302, when the motor 346 rotates the lead screw 348, the lead nut 350 travels linearly along the lead screw 348 thereby driving the lead arm 354 and robotic conditioning arm 302 in a linear direction. As shown by way of example in FIG. 5, the lead screw 348 passes through both the lead nut 350 and the lead arm 354.

Rotating the lead screw 348 in one direction (e.g., clockwise) may linearly drive the robotic conditioning arm 302 forward toward the operative position and away from the non-operative position, and rotating the lead screw 348 in the opposite direction (e.g., counterclockwise) may linearly drive the robotic conditioning arm 302 backward toward the non-operative position and away from the operative position. The motor 346 of the linear actuator 344 may be connected to a controller (not shown), e.g., an intelligent stepper drive controller, that controls operation of the motor 346 in order to move the robotic conditioning arm 302. The controller, in this example, may be connected to and driven by the control module 104 discussed above with reference to FIG. 1.

The linear actuator 344 may be mounted to the mounting frame 304 via a mounting assembly 356. In this example, the mounting assembly 356 includes a collar 358 for the motor 346 of the linear actuator 344 and a lead screw base 360 for the lead screw 348 of the linear actuator 344. As seen in FIG. 5, the collar 358 for the motor 346 includes a central opening 362 for the lead screw 348 to pass through when the collar 358 is attached to the motor 346. The end 364 of the lead screw 348 may be received into the lead screw base 360 in order to secure the lead screw 348. The collar 358 for the motor 346 may be attached to the motor 346 as well as the mounting frame 304 at a collar mount location 366. Similarly, the lead screw base 360 may be attached to the mounting frame 304 at a lead screw base location 368. In this way, the mounting assembly 356 secures the linear actuator 344 to the mounting frame 304.

As mentioned above, the automated conditioning apparatus 300 may aspirate residual fluid from the underside 324 of the patch plate 160 and the top side 326 of the plenum 106. Accordingly, the automated conditioning apparatus 300 may be connected to a plumbing module (370 in FIG. 6) to transport away the aspirated fluid.

Figure 6:
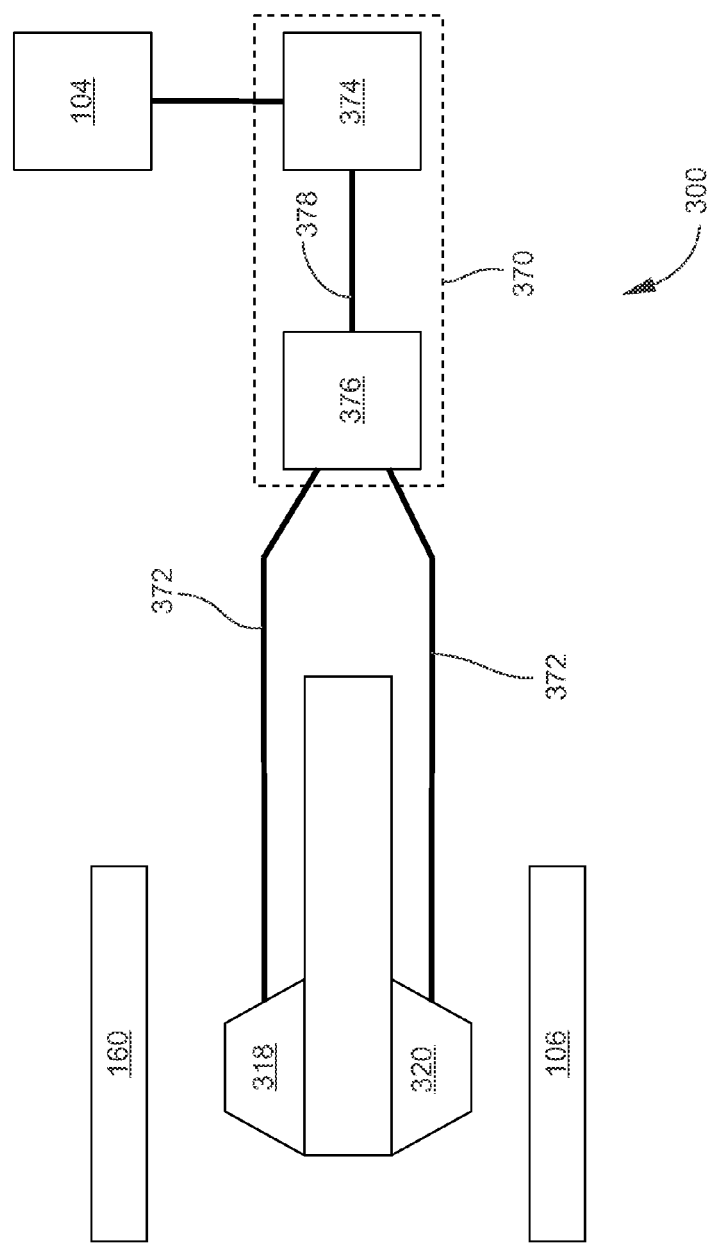
FIG. 6 is a schematic diagram of an example of an implementation of an automated conditioning apparatus connected to a plumbing module.

In FIG. 6, a schematic diagram of an example of an implementation of an automated conditioning apparatus 300 is shown connected to a plumbing module 370. The end effectors 318 and 320 may each be connected to the plumbing module 370 via respective conduit lines 372 as discussed above. The plumbing module 370 may include, for example, a vacuum pump 374 for aspirating the residual fluid from the patch plate 160 and plenum 106 as well as a collection receptacle 376 (e.g., a carboy, vacuum waste bottle, etc.) that receives the aspirated residual fluid. Respective conduit lines 372 may connect the patch plate nozzle 318 and the plenum nozzle 320 to the collection receptacle 376 of the plumbing module 370. A vacuum line 378 may connect the vacuum pump 374 to the collection receptacle 376.

The vacuum pump 374 may be any pump configured to create a vacuum that aspirates the residual fluid from the patch plate 160 or plenum 106 and transports the residual fluid through the vacuum nozzles 318 and 320 (end effectors) and into the collection receptacle 376 via the conduit lines 372. In some example implementations, a diaphragm vacuum pump may be selectively employed.

The vacuum pump 374 may be connected to a control module 104, e.g., the control module 104 of FIG. 1, that controls operation of the vacuum pump 374. The control module 104 may activate the vacuum pump 374 when the end effectors 318 and 320 of the robotic conditioning arm 302 are positioned between the patch plate 160 and plenum 106 to initiate aspiration of the residual fluid. As the linear actuator (344 in FIG. 5) moves the robotic conditioning arm 302 back and forth across the length of the patch plate 160 and plenum 106, the vacuum provided by the vacuum pump 374 aspirates the residual fluid, which is collected in the collection receptacle 376. In some implementations, the vacuum pump 374 may be configured such that the level of vacuum generated thereby (and thus the pressure differential between the respective vacuum nozzles 318 and 320 and the collection receptacle 376) is adjustable, such as in response to an appropriate control signal from the control module 104.

Figure 7A:
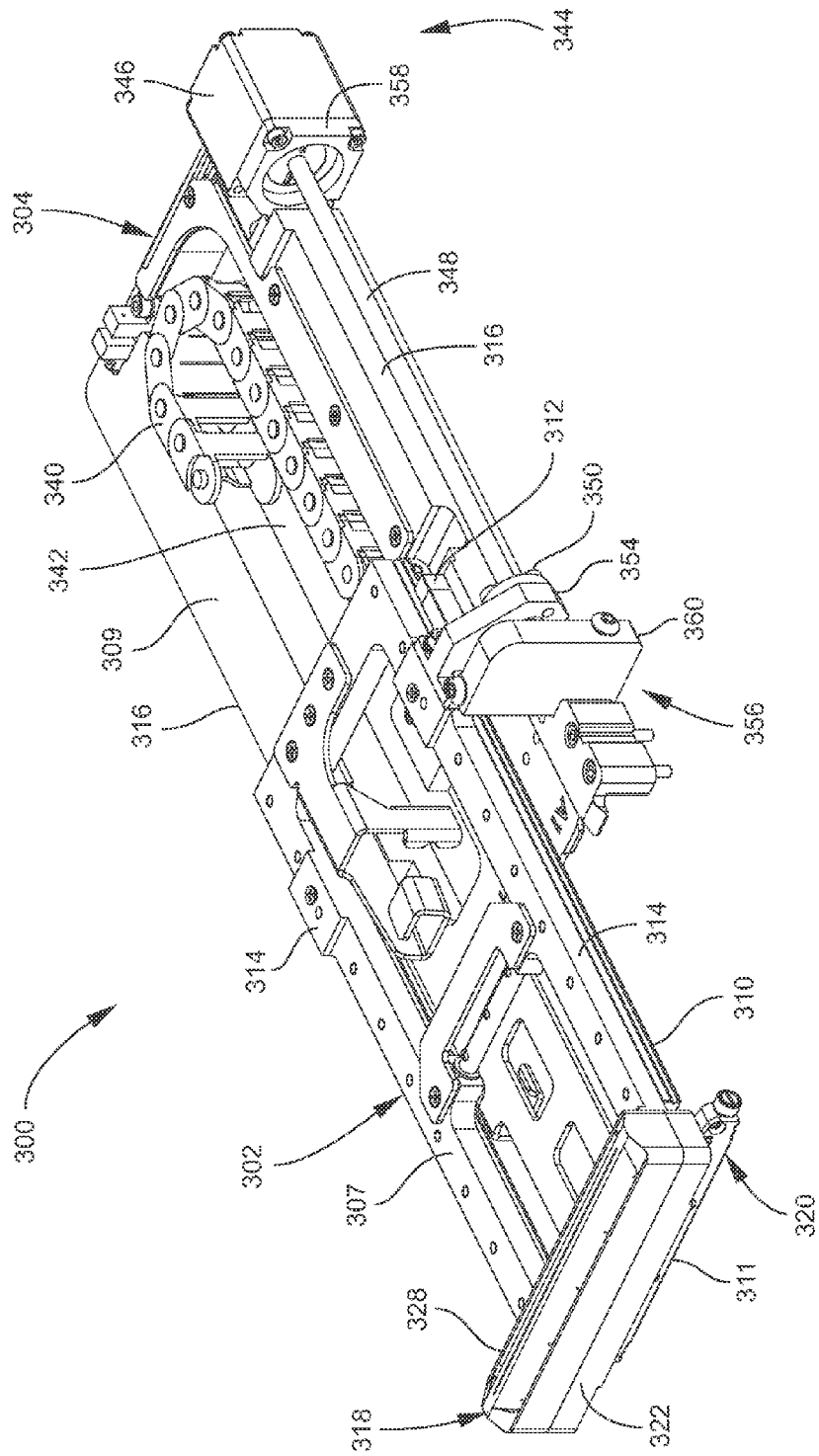
FIG. 7A is a rear top-left perspective view of the automated conditioning apparatus of FIG. 5 shown in an assembled configuration.

Referring now to FIG. 7A, a rear top-left perspective view of the automated conditioning apparatus 300 of FIG. 5 is shown in an assembled configuration. In FIG. 7A, the robotic conditioning arm 302 of the apparatus 300 is shown extended to the operative position. As seen in FIG. 7A, the mounting assembly 356 mounts the linear actuator 344 to the side 316 of the mounting frame 304. The motor 346 of the linear actuator 344 drives the linear movement of the robotic conditioning arm 302 via the lead screw 348, lead nut 350, and lead arm 354, which is mounted to the side 316 of the robotic conditioning arm 302 in this example. Accordingly, the upper end effector 318 and the lower end effector 320, in this example, move in concert with each other since each end effector 318 and 320 is attached to the robotic conditioning arm 302. In some example implementations, the robotic conditioning arm 302 may be configured to independently move the upper end effector 318 and the lower end effector 320 respectively. For example, the robotic conditioning arm 302 may include an upper arm (not shown) and a lower arm (not shown) that are independently movable and controllable.

Also seen in FIG. 7A, the upper end effector 318 (patch plate nozzle) is positioned on the top side 307 of an operative end 322 of the robotic conditioning arm 302 and faces upward toward the underside (324 in FIG. 5) of the patch plate (160 in FIG. 5). The input aperture 328 of the patch plate nozzle 318 receives any residual fluid on the underside 324 of the patch plate 160 during aspiration. The input aperture 328, in this example, is an elongated slit across the width of the patch plate nozzle 318. The length of the input aperture 328 may be substantially similar to the width of the patch plate 160. In this way, the patch plate nozzle 318 may traverse substantially all of the underside 324 of the patch plate 160 as the robotic conditioning arm 302 moves back and forth below the patch plate 160.

In FIG. 7B, a rear bottom-left perspective view of the automated conditioning apparatus 300 of FIG. 5 is shown in an assembled configuration. Like FIG. 7A, the robotic conditioning arm 302 of the automated conditioning apparatus 300 shown in FIG. 7B is extended to the operative position. The lower end effector 320 (plenum nozzle) is positioned on the underside 311 of the operative end 322 of the robotic conditioning arm 302 and faces downward toward the top side (326 in FIG. 5) of the plenum (106 in FIG. 5). As mentioned above, the faceplate 332 and nozzle body 334 of the plenum nozzle 320 may define an input aperture 380 as shown by way of example in FIG. 7B. Like the input aperture (328 in FIG. 7A) of the patch plate nozzle 318, the input aperture 380 of the plenum nozzle 320 is also an elongated slit across the width of the plenum nozzle 320 in this example. The length of the input aperture 380 of the plenum nozzle may be substantially similar to the width of the plenum 106. In this way, the plenum nozzle 320 may traverse substantially all of the top side 326 of the plenum as the robotic conditioning arm 302 moves back and forth above the plenum 106.

Figure 8:
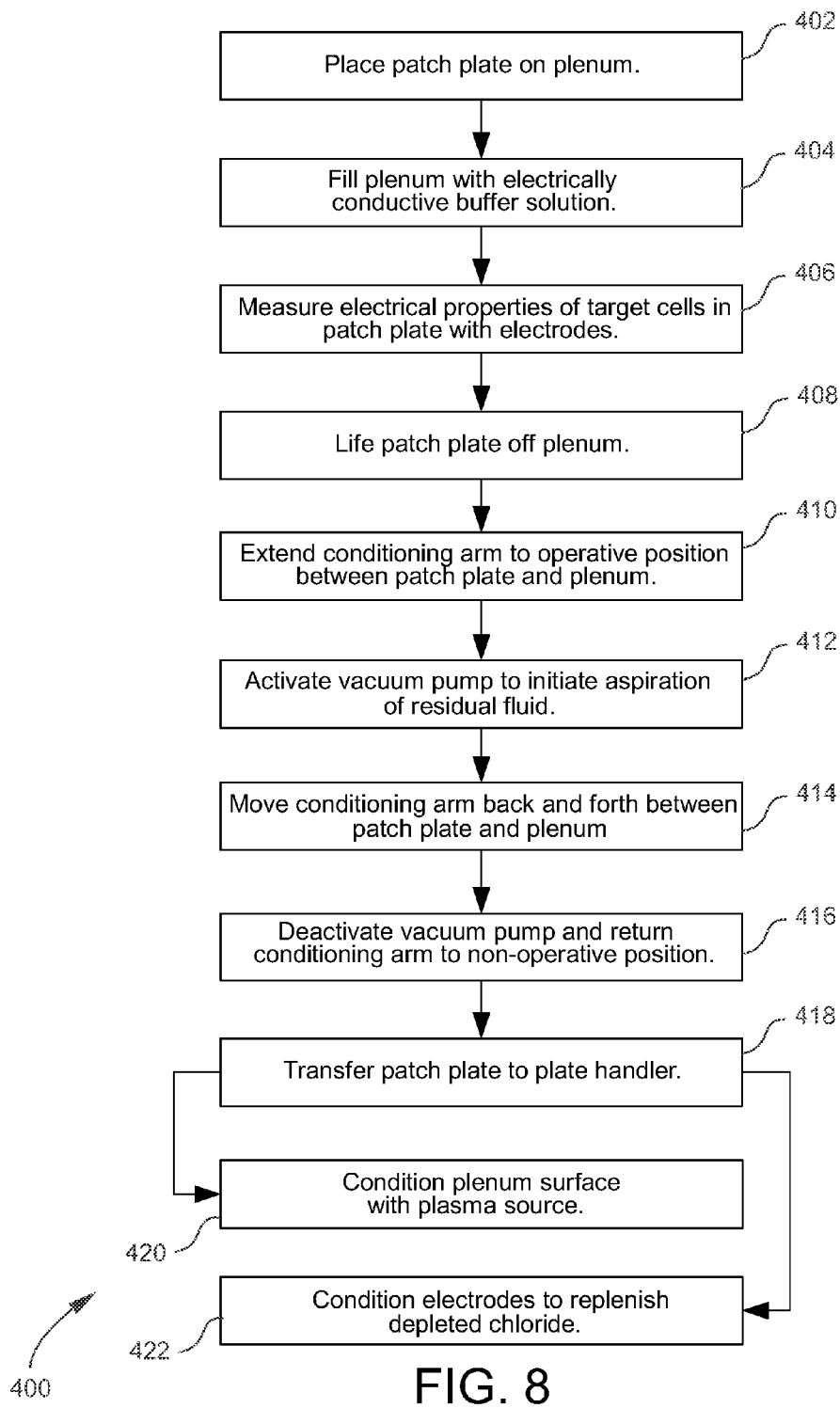
FIG. 8 is a flowchart of example method steps for conditioning a patch plate and plenum of an automated, high-throughput electrophysiology measurement system.

Referring now to FIG. 8, a flowchart 400 of example method steps for conditioning a patch plate and plenum of the automated, high-throughput electrophysiology measurement system is shown. As mentioned above, the automated conditioning apparatus may be used to aspirate residual fluid from a patch plate and plenum following an electrophysiological assay. Accordingly, the patch plate may be placed on the plenum at the start of the assay (step 402), and the plenum may be filled with an electrically conductive buffer solution (step 404). Electrodes of the automated, high-throughput electrophysiology measurement system may measure the electrical properties of target cells in the patch plate during the assay (step 406). When the assay is complete, a robotic pipettor head or a separate robotic plate-handling device may lift the patch plate off the plenum (step 408).

With the patch plate raised above the plenum, the control module may activate the linear actuator to drive the robotic conditioning arm to an operative position between the patch plate and the plenum (step 410). The control module may then activate the vacuum pump to initiate aspiration of the residual fluid (e.g., buffer solution) off the underside of the patch plate and the top side of the plenum (step 412). During aspiration, the control module may control the operation of the linear actuator motor in order to move the conditioning arm back and forth between the patch plate and plenum (step 414). As the conditioning arm moves back and forth, the patch plate nozzle and the plenum nozzle traverse the length of the patch plate and plenum respectively.

When the aspiration process is complete, the control module may deactivate the vacuum pump and instruct the linear actuator motor to drive the conditioning arm back to the non-operative position (step 416). Once the residual fluid has been removed from the underside of the patch plate, the patch plate may be safely transferred to a robotic plate handler (step 418).

The robotic conditioning arm may be configured to perform other types of conditioning beyond aspiration of residual fluid. For example, the robotic conditioning arm may be configured to condition the surface of the plenum with plasma in order to change the surface properties of the plenum (step 420), and/or condition the ground electrodes of the plenum (step 422) by removing excess chloride from the ground electrodes.

Figure 9:
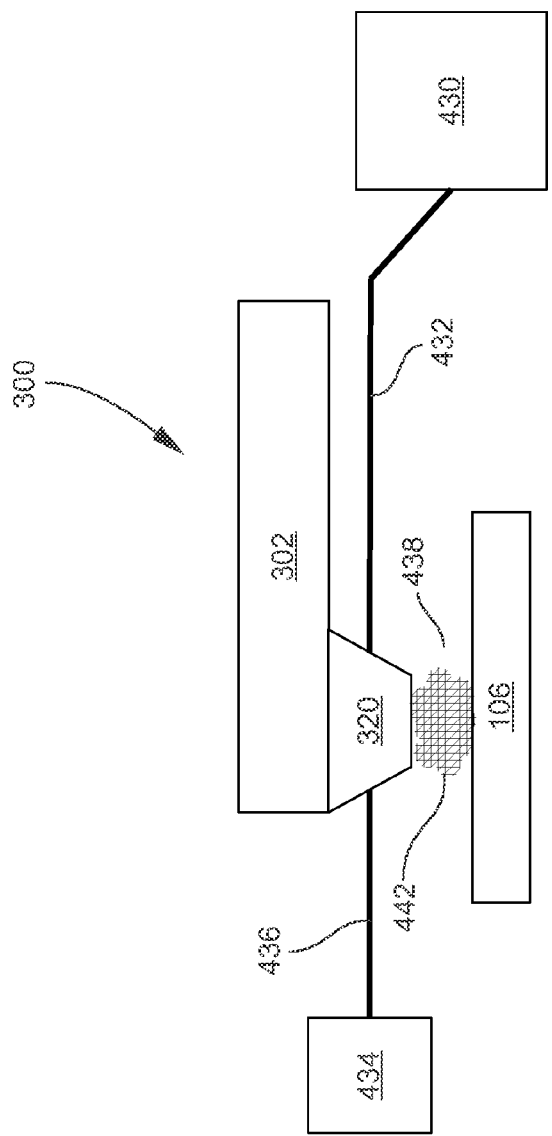
FIG. 9 is a schematic diagram of an example of an implementation of an automated conditioning apparatus configured for plenum surface conditioning

In some example circumstances, between assays it may be desirable to clean one or more surfaces of the plenum, change the surface properties of the plenum between assays (e.g., to make the surface of the plenum more hydrophilic), or otherwise treat one or more surfaces of the plenum. For example, imparting or increasing the hydrophilicity of plenum surfaces may improve assay performance by, for example, enabling a more complete fluid exchange in the plenum. Referring to FIG. 9, a schematic diagram of an example of an implementation of an automated conditioning apparatus 300 configured for plenum surface conditioning is shown. The lower end effector 320, in this example, is an atmospheric-pressure plasma head communicating with a gas source 430 via a gas line 432 and a power source 434 via a power cable 436. The power source 434, in this example, is a DC power source. Once the desired gas has been delivered to the region 438 in between the plasma head 320 and the plenum 106 via a gas line 432, the power source 434 is used to ionize the gas and create the plasma 440. The plasma 440 will then condition the surface 442 of the plenum 106 as shown by way of example in FIG. 9. In order to ignite the gas into plasma, the gas may be immersed in an electric field between the plasma head 320 and the surface 442 of the plenum 106. A voltage may be applied across a pair of electrodes spaced apart from each other to create the electric field. One of the electrodes may be, for example, the plasma head 320, which may include a metal housing (not shown) that contains the gas. The other electrode may be, for example, the ground electrodes (130 in FIG. 1) at the plenum 106 or, alternatively, a metal insert grid (not shown) at the plenum 106. The metal insert grid may lay over the plenum 106 within close proximity to the surface 442 of the plenum 106 (e.g., 50-100 mm). As an additional alternative, the two electrodes that create the electric field may reside within the plasma head 320 in order to create the electric field within the plasma head 320. In this alternative example, the plasma may be ignited within the plasma head 320 and continued flow from the gas source 430 may direct the plasma out of the plasma head 320 toward the plenum through a wide nozzle (not shown), i.e., a plasma jet similar to a torch.

As appreciated by persons skilled in the art, the composition of the gas supplied by the gas source 430, and thus the active species comprising the plasma 440, will depend on the type of plasma treatment desired. Examples of gases may include, but are not limited to, air, oxygen, nitrogen, hydrogen, argon, and helium. The active species desired to interact with the plenum surface(s) 442 may include, but are not limited to, metastables, ions, species in a Rydberg state, free electrons, free radicals, and other energized and/or reactive species. As appreciated by persons skilled in the art, additives may be added to the background gas as needed to effect a desired interaction between the plasma 440 and the plenum surface(s) 442 exposed thereto. Moreover, in other implementations the plasma head 320 may be configured for producing a plasma 440 powered by an AC (Alternating Current) power source such as, for example, a dielectric barrier discharge.

Figure 10:
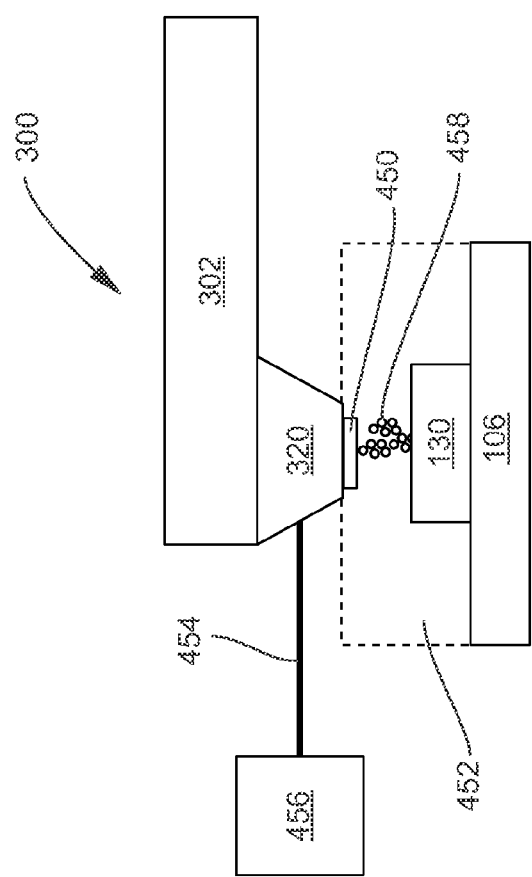
FIG. 10 is a schematic diagram of an example of an implementation of an automated conditioning apparatus configured to condition the electrodes of a plenum

In other example circumstances, it may be desirable to remove excess chloride that has accumulated on the ground electrodes (130 in FIG. 1) of the plenum (106 in FIG. 1) over time as a result of performing electrophysiological assays that entail the use of Ag/AgCl sense electrodes (132 in FIG. 1). The robotic conditioning arm 302 may be configured to remove excess chloride from the ground electrodes 130. Referring to FIG. 10, a schematic diagram of an example of an implementation of an automated conditioning apparatus 300 configured to condition the electrodes 130 of a plenum 106 is shown. For example, assume the electrode 130 in the plenum 106 is an anode and has a build-up of excess chloride. In order to condition this electrode 130, the surplus chloride may be removed. The lower end effector 320, in this example, is an electrode conditioner. A cathode 450 (e.g., silver chloride) is attached to the underside of the electrode conditioner 320 such that the cathode 450 is submerged in an electrically conductive solution 452 contained in the plenum 106. The electrode conditioner 320 is connected via a power cable 454 to a power source 456 that applies a voltage potential to the electrode conditioner 320 relative to the anode 130. The voltage potential causes chloride atoms 458 to disassociate from the anode 130 as chloride anions 458. The chloride anions 458 travel through the conductive solution 452 and bond with the cathode 450. In this way, the robotic conditioning arm 302 may be employed to periodically deplete excess chloride from the ground electrodes 130.

It will be understood that the automated conditioning apparatus 300 may be selectively employed to condition only the plenum (106 in FIG. 5) or only the patch plate (160 in FIG. 5). In this regard, in some example implementations, an automated conditioning apparatus 300 may only include one end effector 318 or 320, e.g., an upper end effector 318 or a lower end effector 320 as shown by way of example in FIGS. 6 and 9-10. Moreover, the lower end effector 320 may function to aspirate fluid, apply plasma (440 in FIG. 9), and/or condition one or more ground electrodes (130 in FIG. 10) of the plenum 106, as described above. In other implementations, a plurality of lower (or second) end effectors 320 may be included to provide different types of conditioning. As examples, the second end effector 320 may include a vacuum nozzle for aspiration and a third end effector may include a plasma head or an electrode conditioner. Alternatively, third and fourth end effectors may respectively include a plasma head and an electrode conditioner.

As mentioned above, a robotic plate handler may transfer the patch plate 160 (or other component) to other locations in the electrophysiology measurement system (100 in FIG. 1). As the plate handler moves the patch plate 160, however, offset errors relating to the desired orientation of the patch plate 160 (or other component) may occur and accumulate. Additionally, in some circumstances, it may be desirable to rotate the patch plate 160 to one or more different angular positions relative to an initial position. Accordingly, an automated high-throughput electrophysiology measurement system 100 may include an automated reorientation apparatus to reorient the patch plate 160 or other similarly-sized components.

Figure 11:
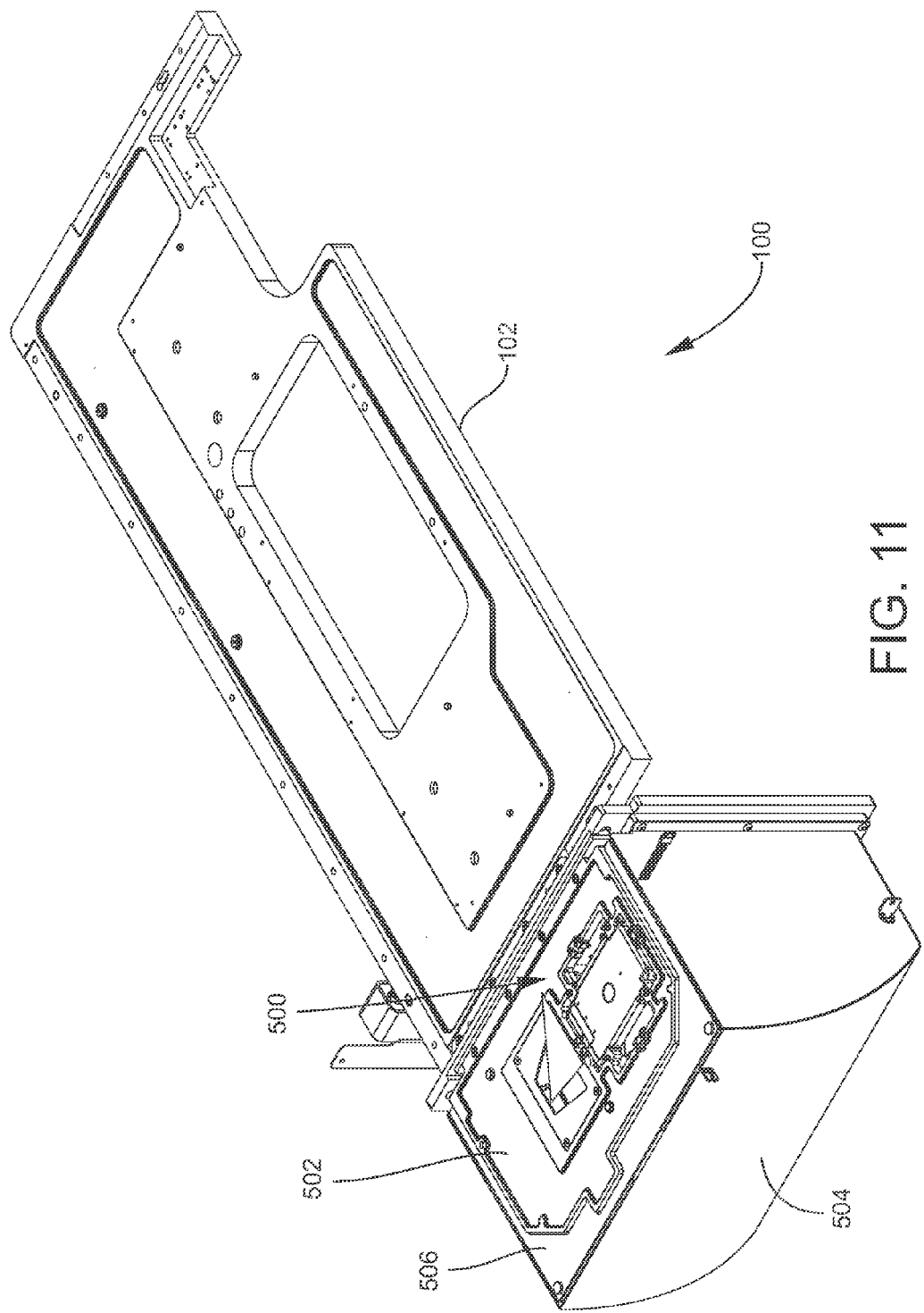
FIG. 11 is a front top-left perspective view of an example of an implementation of an automated reorientation apparatus installed next to the process deck of an automated, high-throughput electrophysiology measurement system.

Referring to FIG. 11, a front top-left perspective view of an example of an implementation of an automated reorientation apparatus 500 for an automated, high-throughput electrophysiology measurement system (100 in FIG. 11) is shown. The automated reorientation apparatus 500 may reside, for example, at a landing pad 502 that is situated next to the process deck 102 of the automated, high-throughput electrophysiology measurement system 100. One or more components of the automated reorientation apparatus 500 may reside within a landing pad housing 504 and underneath the top side 506 of the landing pad 502. As mentioned above, a robotic plate handler may transfer a patch plate 160 (or other similarly-sized component) to the landing pad 502 (or a user may manually load a patch plate 160 at the landing pad 502), and the automated reorientation apparatus 500 may correct any offset errors or rotate the patch plate 160 to a new orientation.

Figure 12:
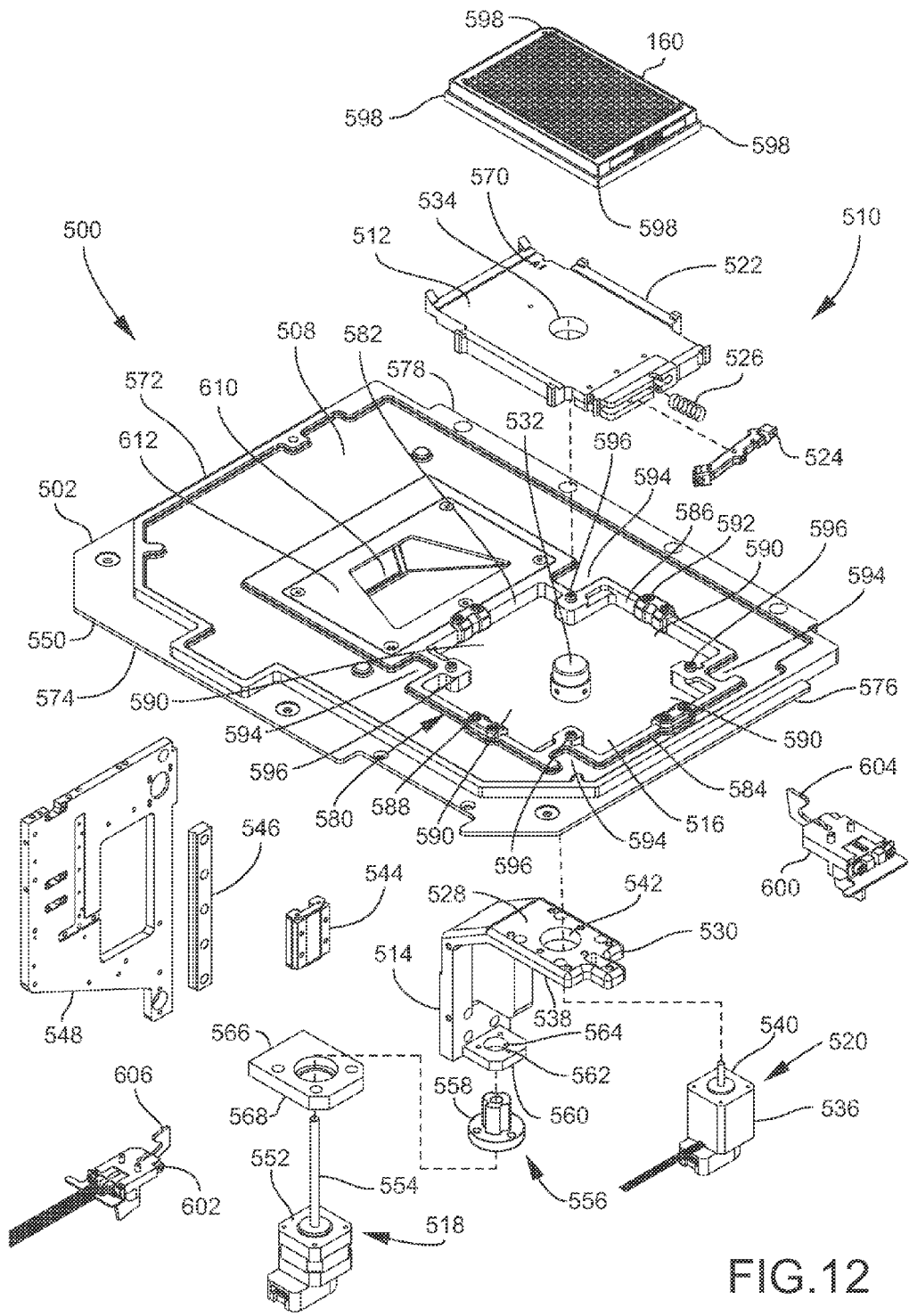
FIG. 12 is an exploded view of the automated reorientation apparatus of FIG. 11.

Referring to FIG. 12, an exploded view of the automated reorientation apparatus 500 of FIG. 11 is shown. In this example, the components of the automated reorientation apparatus 500 may be mounted to an upper mounting frame 508 of the landing pad (502 in FIG. 11).

In the illustrated example, the automated reorientation apparatus 500 includes a linearly displaceable platform 510 configured to support a patch plate 160 (or other transportable component) on an upper surface 512 of the platform 510. The linearly displaceable platform 510, in this example, may also be configured to rotate 360° about a central axis relative to the mounting frame 508 of the landing pad 502. Accordingly the platform 510 may also be referred to as a turntable assembly ("turntable"). The turntable 510 may be mounted to an elevating arm 514 that moves the turntable 510 through a turntable opening 516 formed through the mounting frame 508. The elevating arm 514 may raise and lower the turntable 510 between a raised position above the mounting frame 508 and a lowered position below the mounting frame 508. The elevating arm 514 may also raise or lower the turntable 510 such that the turntable 510 is situated within the turntable opening 516 formed through the mounting frame 508. A linear actuator 518 drives the movement of the elevating arm 514 up and down relative to the mounting frame 508, and a rotary actuator 520 drives rotation of the turntable 510.

The turntable 510, in this example, includes a turntable body 522 that supports a patch plate 160 (or other component for which transport is desired, which may have the same or similar footprint as a patch plate 160), a pivotable cornering arm 524 for adjusting the position of a patch plate 160 resting on the turntable body 522, and a spring 526 for biasing the pivotable cornering arm 524. These components of the turntable 510 will be discussed in further detail below with reference to FIGS. 14-15.

The turntable 510 is also connected to the elevating arm 514 such that the elevating arm 514 may raise and lower the turntable 510. The turntable 510, in this example, is mounted to the top side 528 of an upper flange 530 of the elevating arm 514. The turntable 510, in this example, is connected to the rotary actuator 520 via a rotary shaft 532, which is mounted within an opening 534 formed through the center of the turntable body 522. The rotary actuator 520 includes a motor 536 that drives rotation of the rotary shaft 532 thus rotating the turntable 510.

The rotary actuator 520, in this example, is mounted to the underside 538 of the upper flange 530 of the elevating arm 514. The rotor 540 of the motor 536 of the rotary actuator 520 may pass through an opening 542 formed through the upper flange 530 of the elevating arm 514 to engage the rotary shaft 532 as shown by way of example in FIG. 12. The elevating arm 514 may raise the turntable 510 above the mounting frame 508 of the landing pad 502 such that the rotary actuator 520 may rotate the turntable 510 above the mounting frame 508 of the landing pad 502. Similarly, the elevating arm 514 may lower the turntable 510 below the mounting frame 508 of the landing pad 502 such that the rotary actuator 520 may rotate the turntable 510 below the mounting frame 508 of the landing pad 502.

The turntable 510 may be rotated in one direction (e.g., clockwise) by having the motor 536 rotate the rotor 540 in the desired direction. The turntable 510 may be rotated in the opposite direction (e.g., counterclockwise) by having the motor 536 rotate the rotor 540 in the opposite direction. The rotary actuator 520 may rotate the turntable 510 a full 360°. Accordingly, rotating the turntable 510 90° may be referred to as a quarter turn; rotating the turntable 510 180° may be referred to as a half turn; and rotating the turntable 510 270° may be referred to as a three-quarter turn. The motor 536 of the rotary actuator 520 may be connected to a controller (not shown), e.g., an intelligent stepper drive controller, that controls operation of the motor 536 in order to rotate the turntable 510. The controller, in this example, may be connected to and driven by the control module 104 discussed above with reference to FIG. 1.

The elevating arm 514, in this example, is mounted to a guide block 544, which engages a guide rail 546 in a tongue-and-groove fashion. The guide rail 546 is mounted to a vertical mounting wall 548, which is mounted to the underside 550 of the mounting frame 508 as shown by way of example in FIG. 12. In this way, the elevating arm 514 may slide vertically along the guide rail 546 when raising and lowering the turntable 510.

The linear actuator 518 drives the elevating arm 514 up and down to raise and lower the turntable 510 as described. The linear actuator 518, in this example, includes a motor 552 connected to a lead screw 554 that engages a lead nut 556, which is mounted to the elevating arm 514. As shown by way of example in FIG. 12, the lead nut 556 includes a flange 558 that is mounted to the underside 560 of a lower flange 562 of the elevating arm 514 such that the lead nut 556 extends through an opening 564 formed through the lower flange 562 of the elevating arm 514.

The motor 552 of the linear actuator 518 may be a stepper motor (e.g., a Nema 11 stepper motor) and rotate the lead screw 554. The lead screw 554, in this example, includes threads that engage threads on the inner surface of the lead nut 556. Because the lead nut 556 is mounted to the elevating arm 514, when the motor 552 of the linear actuator 518 rotates the lead screw 554, the lead nut 556 travels along the lead screw 554 thereby driving the elevating arm 514 in a linear direction. As seen in FIG. 12, the lead screw 554 passes through both the lead nut 556 and the opening 564 formed through the lower flange 562 of the elevating arm 514.

Rotating the lead screw 554 in one direction (e.g., clockwise) may linearly drive the elevating arm 514 upward, and rotating the lead screw 554 in the opposite direction (e.g., counterclockwise) may linearly drive the elevating arm 514 downward. The motor 552 of the linear actuator 518 may be connected to a controller (not shown), e.g., an intelligent stepper drive controller, that controls operation of the motor 552 in order to raise and lower the elevating arm 514. The controller, in this example, may be connected to and driven by the control module 104 discussed above with reference to FIG. 1.

The linear actuator 518, in this example, may also be mounted to the vertical mounting wall 548. A mounting block 566 may mount the linear actuator 518 to the mounting wall 548. The mounting block 566 may include an opening 568 that the lead screw 554 passes through in order to engage the lead nut 556 as shown by way of example in FIG. 12.

As the elevating arm 514 raises and lowers the turntable 510, the turntable passes through the opening 516 formed through the mounting frame 508 of the landing pad 502. Accordingly, the turntable opening 516 is sized and shaped to permit movement of the turntable 510 through the opening 516. The turntable opening 516, in this example, has a cruciform shape in order to receive the turntable 510 in a portrait orientation or a landscape orientation. In this example, a portrait orientation refers to an orientation of 0° or 180° relative to the mounting frame 508 of the landing pad 502, and a landscape orientation refers to an orientation of 90° or 270° relative to the mounting frame 508 of the landing pad 502.

The turntable 510 may include a reference corner 570 (e.g., the "A1" corner) that may be used when identifying the orientation of the turntable 510 relative to the mounting frame 508 of the landing pad 502. In FIG. 12, the reference corner 570 of the turntable 510 (the "A1" corner) corresponds to the top edge 572 of the mounting frame 508; therefore, the turntable 510 shown in FIG. 12 is oriented at 0° relative to the mounting frame 508. The other orientations may proceed, for example, counterclockwise around the edges 574, 576, and 578 of the mounting frame 508. In the example shown in FIG. 12, a 0° orientation corresponds to the top edge 572 of the mounting frame 508; a 90° orientation corresponds to the left edge 574 of the mounting frame 508; a 180° orientation corresponds to the bottom edge 576 of the mounting frame 508; and a 270° orientation corresponds to the right edge 578 of the mounting frame 508.

The opening 516 of the mounting frame 508 defines an interior edge 580 that circumscribes the opening 516. Due to the cruciform shape of the opening 516 of the mounting frame 508, in this example, the opening 516 defines a pair of lateral interior edges 582 and 584—the top interior edge 582 and the bottom interior edge 584—and a pair of longitudinal interior edges 586 and 588—the right interior edge 586 and the left interior edge 588. A respective cornering cam 590 is attached to each interior edge 582, 584, 586, and 588 of the turntable opening 516 in this example. As seen in FIG. 12, the turntable opening 516 includes four cornering cams 590 respectively attached to (or otherwise mounted proximate to) the top interior edge 582, the left interior edge 588, the bottom interior edge 584, and the right interior edge 586 of the turntable opening 516. Also seen in FIG. 12, the cornering cams 590 each include a beveled edge 592 (e.g., a 45° beveled edge). The cornering cams 590, in this example, engage the cornering arm 524 of the turntable 510 in order to push a patch plate 160 supported on the turntable 510 toward the reference corner 570. In this way, the automated reorientation apparatus 500 may correct for any offset errors that accumulate during handling of the patch plate 160. Offset correction using the cornering arm 524 and cornering cams 590 will be discussed in further detail below.

The cruciform shape of the turntable opening 516, in this example, results in four interior corners 594 positioned around the turntable opening 516 at the top-right, top-left, bottom-left, and bottom-right of the turntable opening 516 respectively. Each interior corner 594, in this example, includes a support column 596 for supporting the patch plate 160 or other similarly-sized component. The turntable opening 516 may include four support columns 596 respectively corresponding to the four corners 598 of the patch plate 160 as shown by way of example in FIG. 12. As discussed in further detail below, the turntable 510 may deposit the patch plate 160 onto the support columns 596 as the elevating arm 514 lowers the turntable 510 through the turntable opening 516.

A pair of patch plate detection assemblies 600 and 602 may also be mounted to the underside 550 of the mounting frame 508. The plate detection assemblies 600 and 602 may be used to identify whether a patch plate 160 is oriented in a portrait or landscape orientation when the turntable 510 deposits the patch plate 160 onto the support columns 596 of the turntable opening 516. As shown by way of example in FIG. 12, each patch plate detection assembly 600 and 602 includes a respective displaceable tab 604 and 606. The patch plate detection assemblies 600 and 602 may be mounted to the underside 550 of the mounting frame 508 such that the displaceable tabs 604 and 606 are respectively situated next to one of the support columns 596 at the turntable opening 516.

In order to detect a patch plate 160 in a portrait orientation (i.e., 0° or 180°), for example, one of the patch plate detection assemblies 600 may be mounted under the bottom edge 584 of the turntable opening 516 such that the tab 604 is positioned to the right of the bottom-right support column 596. Accordingly, a patch plate 160 resting on the support columns 596 in a portrait orientation would displace the tab 604 of the plate detection assembly 600. In response to displacement of the tab 604, the plate detection assembly 600 may generate a signal and transmit the signal to a control module (not shown), e.g., the control module 104 of FIG. 1. In response to receipt of the signal from the plate detection assembly 600, the control module may determine that the patch plate 160 is oriented in a portrait orientation.

Similarly, in order to detect a patch plate 160 in a landscape orientation (i.e., 90° or 270°), another patch plate detection assembly 602 may be mounted, for example, under the left edge 588 of the turntable opening 516 such that the tab 606 is positioned next to the bottom-left support column 596. Accordingly, a patch plate 160 resting on the support columns 596 in a landscape orientation would displace the tab 606 of the plate detection assembly 602, which may generate a signal in response and transmit the signal to a control module (not shown), e.g., the control module 104 of FIG. 1. In response to receipt of the signal from the plate detection assembly 602, in this example, the control module may determine that the patch plate 160 is oriented in a landscape orientation.

The landing pad (502 in FIG. 11) of an automated, high-throughput electrophysiology measurement system (100 in FIG. 11) may include a barcode reader 610 for reading a barcode (not shown) applied to one of the sides of the patch plate 160 or other similarly-sized components. As seen in FIG. 12, the barcode reader 610 may be positioned below the mounting frame 508 of the landing pad 502. The barcode reader 610 may direct an infrared beam upward through an opening 612 formed through the mounting frame 508 in order to read barcodes applied to the sides of patch plates 160. The elevating arm 514 may raise the turntable 510 above the mounting frame 508 such that the sides of a patch plate 160 cross the path of the beam from the bar code reader 610. Because barcodes may not be applied to the sides of patch plates 160 at a standard location, the rotary actuator 520 may rotate the turntable 510 such that the side of the patch plate 160 that includes the barcode is brought into view of the barcode reader 610.

Figure 13A:
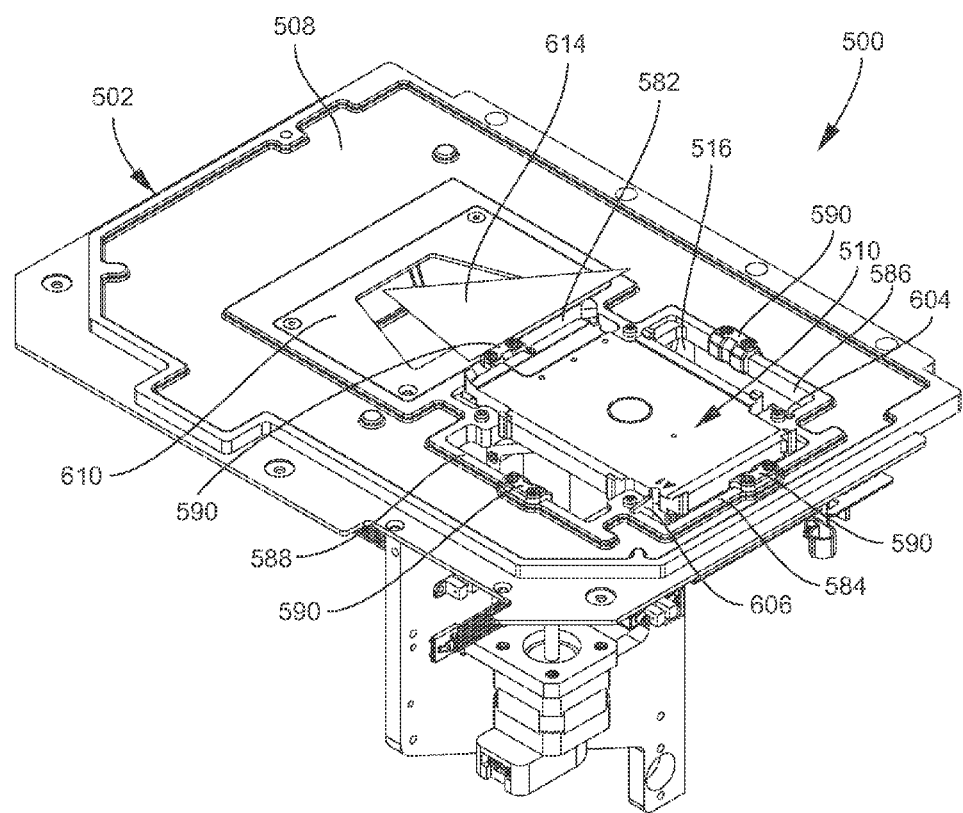
FIG. 13A is a top-left perspective view of the automated reorientation apparatus of FIG. 12 shown in an assembled configuration

FIG. 13A is a top-left perspective view of the automated reorientation apparatus 500 of FIG. 12 shown in an assembled configuration. In FIG. 13A, the turntable 510 is raised slightly above the mounting frame 508 of the landing pad 502 within view of the barcode reader 610. Accordingly, an infrared beam 614 from the barcode reader 610 may read a barcode (not shown) applied to one of the sides of a patch plate (160 in FIG. 12) resting on the turntable 510. If the barcode is not within view of the barcode reader 610, the rotary actuator (520 in FIG. 12) may rotate the turntable 510 to bring the side of the patch plate 160 with the barcode into view of the barcode reader 610. In FIG. 13A, the turntable 510 is oriented at a 270° orientation relative to the mounting frame 508 with the reference corner 570 positioned next to the bottom interior edge 584 of the turntable opening 516. Also seen in FIG. 13A, the cornering cams 590 are respectively attached to respective interior edges 582, 584, 586, and 588 of the turntable opening 516. Additionally, the tabs 604 and 606 of the patch plate detection assemblies (600 and 602 in FIG. 12) are seen respectively positioned next to the bottom-right support column 596 and the bottom-left support column 596.

Figure 13B:
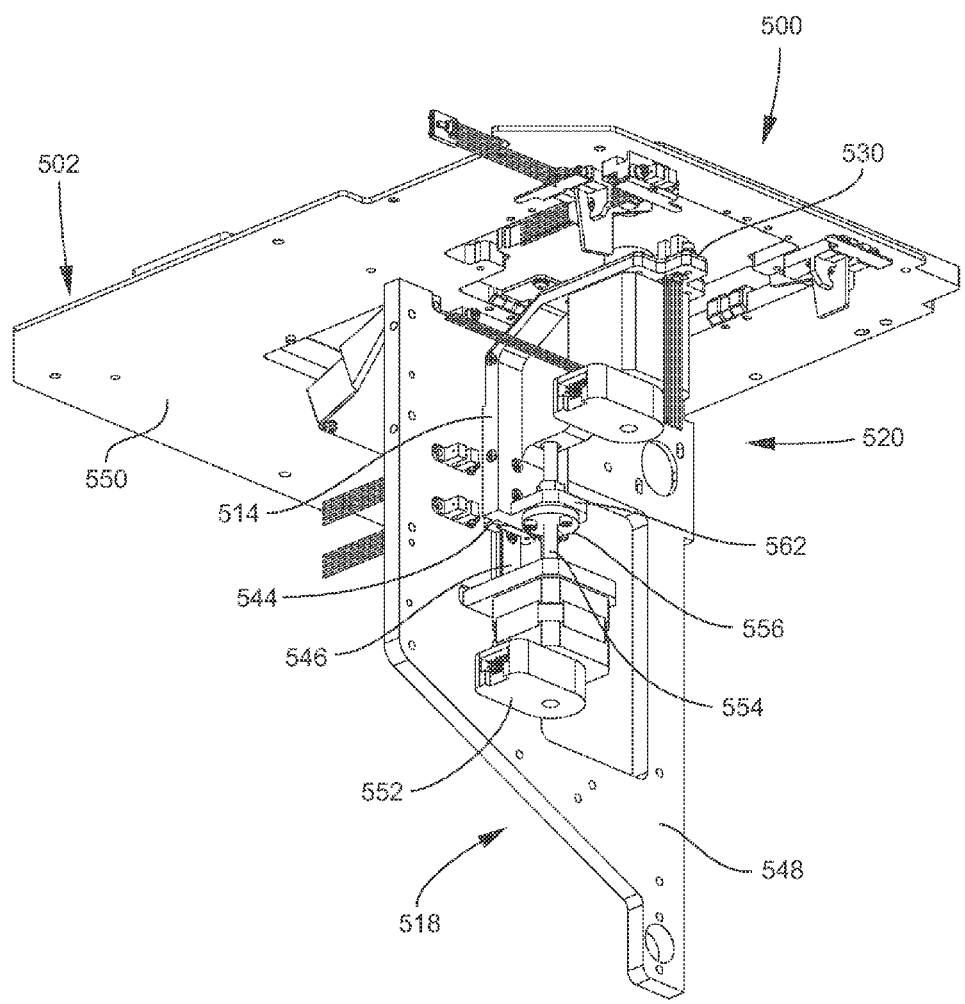
FIG. 13B is a bottom-left perspective view of the automated reorientation apparatus of FIG. 12 shown in an assembled configuration.

FIG. 13B is a bottom-left perspective view of the automated reorientation apparatus 500 of FIG. 12 shown in an assembled configuration. In this example, the vertical mounting wall 548 is secured to the underside 550 of the landing pad 502 mounting frame 508. The guide rail 546 and guide block 544 are secured to the vertical mounting wall 548. The guide block 544 engages the guide rail 546 and is secured to the elevating arm 514. The motor 552 of the linear actuator 518 is secured to the underside of the mounting block 566, and the lead screw 554 passes through the lead nut 556, which is secured to and passes through the lower flange 562 of the elevating arm 514. The rotary actuator 520 is secured to the underside of the upper flange 530 of the elevating arm 514. An elevator arm housing (not shown) may surround the elevating arm 514 and rotary actuator 520 to protect these components.

Figure 14:
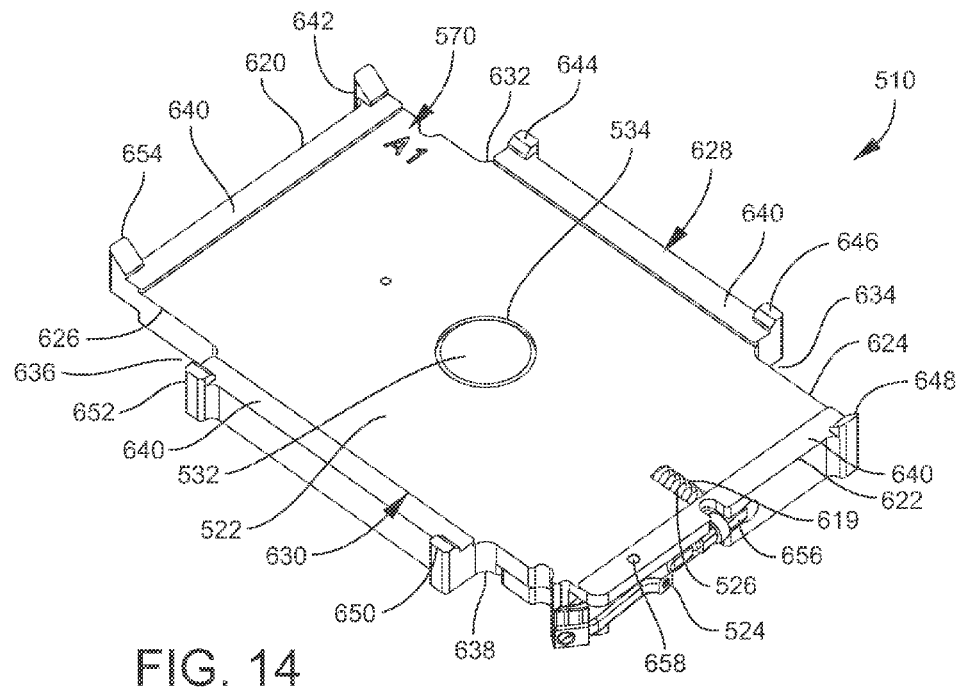
FIG. 14 is a perspective view of an example of an implementation of a turntable assembly of an automated reorientation apparatus.

Referring now to FIG. 14, a perspective view of an example of an implementation of a turntable assembly 510 ("turntable") of an automated reorientation apparatus (500 in FIG. 12) is shown. As mentioned above, the turntable 510 includes a turntable body 522, a biasing spring 526 housed in a recess 619, and a pivotable cornering arm 524. The turntable 510 also includes a reference corner 570 that may be used when adjusting a patch plate (160 in FIG. 12) in order to correct for accumulated offset errors. The reference corner 570, in this example, is located at the top-left corner of the turntable 510 marked "A1." As mentioned above, an opening 534 may be formed through the center of the turntable body 522 in which a rotary shaft 532 is mounted in order to connect the turntable 510 to the rotary actuator (520 in FIG. 12).

The turntable body 522 may have a size and shape substantially similar to that of the patch plate 160 in order to support the patch plate 160. For example, the turntable body 522, in this example, has a substantially rectangular shape. Accordingly, the turntable body 522 may be described as having a pair of lateral edges 620 and 622, a left lateral edge 620 and a right lateral edge 622, and a pair of longitudinal edges 624 and 626, a top longitudinal edge 624 and a bottom longitudinal edge 626. The turntable body 522 may also have a length and width similar to the length and width of the patch plate 160.

The turntable body 522, in this example, includes a pair of elongated wings 628 and 630 at each respective longitudinal edge 624 and 626. In this example, a top wing 628 extends away from the top longitudinal edge 624, and a bottom wing 630 extends away from the bottom longitudinal edge 626. Each end of the wings 628 and 630 may thus form respective exterior corners 632, 634. 636, and 638 with the longitudinal edges 624 and 626 where the wings 628 and 630 meet the respective longitudinal edges 624 and 626. As seen in FIG. 14, the top wing 628 forms a top-left exterior corner 632 and a top-right exterior corner 634. Similarly, the bottom wing 630 forms a bottom-left exterior corner 363 and a bottom-right exterior corner 638. The exterior corners 623, 634, 636, and 638 of the turntable body 522 have a shape substantially similar to the support columns (596 in FIG. 12) of the turntable opening (516 in FIG. 12) at the mounting frame 508 of the landing pad 502. In this way, the exterior corners 623, 634, 636, and 638 may receive the support columns 596 of the turntable opening 516 when the turntable 510 passes through the turntable opening 516 as it raises and lowers.

As mentioned above, the width of the turntable body 522 may be substantially similar to that of a patch plate 160. In this example, the width, $w_1$, of the turntable body 522 between the wings 628 and 630 is substantially similar to the width of the patch plate 160, while the width, $w_2$, of the turntable body 522 not between the wings 628 and 630 is slightly less than the width of the patch plate 160 as seen in FIG. 14, i.e., $w_1 > w_2$. Due to this configuration of the turntable body 522, the corners (598 in FIG. 12) of the patch plate 160 hang over the exterior corners 632, 634, 636, and 638 of the turntable body 522. As a result, the support columns 596 of the turntable opening 516 engage the corners 598 of the patch plate 160 as the turntable 510 lowers through the turntable opening 516 thereby depositing the patch plate 160 onto the support columns 596.

The turntable body 522 may also include raised lips 640 along each of the lateral edges 620 and 622 and the elongated wings 628 and 630. A patch plate 160 may rest on these raised lips 640 when the patch plate 160 is deposited onto the turntable 510. The lateral edges 620 and 622 and elongated wings 628 and 630 may also include upward-projecting bosses 642, 644, 646, 648, 650, 652, and 654 to restrain movement of a patch plate 160 resting on the turntable 510. The turntable body 522, in this example, includes a pair of bosses 644 and 646 positioned at each end of the top elongated wing 628, a pair of bosses 650 and 652 positioned at each end of the bottom elongated wing 630, and a pair of bosses 642 and 654 positioned at each end of the left lateral edge 620. The right lateral edge 622 of the turntable body 522, in this example, only includes a boss 648 positioned the top end of the lateral edge 622 opposite the cornering arm 524.

At the bottom end of the right lateral edge 622, a cornering arm 524 may pivot toward and engage a patch plate 160 resting on the turntable 510. As seen in FIG. 14, the cornering arm 524 resides within an elongated recess 656 formed in the right lateral edge 622 of the turntable body 522. A pivot pin 658 attaches the cornering arm 524 to the turntable body 522 thereby enabling the cornering arm 524 to pivot towards or away from the turntable body 522. As seen in FIG. 14, the pivot pin 658 attaches the center of the cornering arm 524 to the turntable body 522. Accordingly, when one end of the cornering arm 524 moves toward the turntable body 522, the other end of the cornering arm 524 moves away from the turntable body 522.

Figure 15:
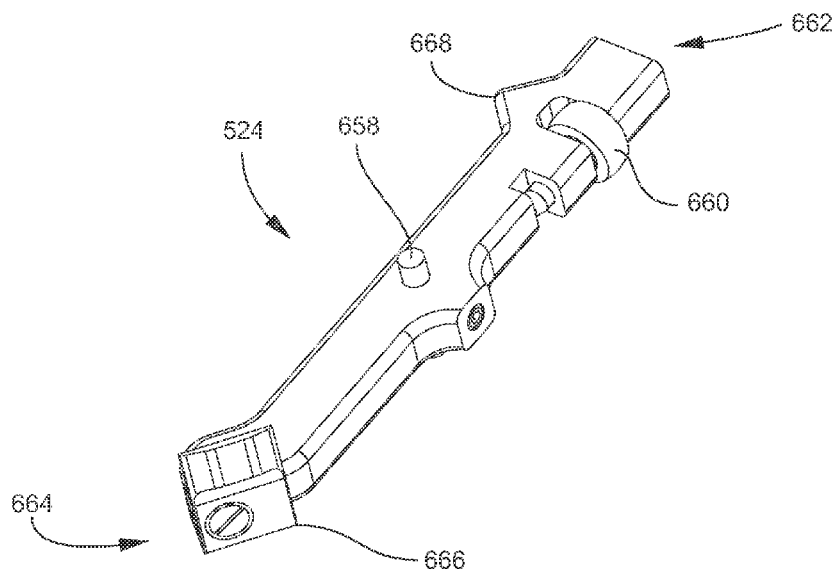
FIG. 15 is perspective view of an example of an implementation of a cornering arm for a turntable of an automated reorienting apparatus.

With additional reference to FIG. 15, an example of an implementation of a cornering arm 524 for a turntable (510 in FIG. 14) of an automated reorientation apparatus (500 in FIG. 12) is shown. The cornering arm 524 is used to adjust the position of a patch plate (160 in FIG. 12) resting on the turntable 510 in order to correct for offset errors accumulated during handling of the patch plate 160. The cornering arm 524, in this example, includes a cam follower 660 that engages the cornering cams (590 in FIG. 12) positioned at the respective interior edges (582, 584, 586, and 588 in FIG. 12) of the turntable opening (516 in FIG. 12) in the mounting frame (508 in FIG. 12) of the landing pad (502 in FIG. 12). Accordingly, the end 662 of the cornering arm 524 having the cam follower 660 may be referred to as the cam-engagement end 662 of the cornering arm 524. The cam follower 660 may be, for example, a rolling wheel to facilitate movement past the cornering cam 590 while the cam follower 660 is engaged with the cornering cam 590.

At the opposite end 664 of the cornering arm 524, in this example, the cornering arm 524 includes a bumper 666 that engages a corner (598 in FIG. 12) of a patch plate 160 resting on the turntable 510. Accordingly, the end 664 of the cornering arm 524 having the bumper 666 may be referred to as the plate-engagement end 664. As seen in FIG. 14, the bumper 666 is positioned next to the bottom-right corner of the turntable body (522 in FIG. 14). As the bumper 666 moves toward the turntable body 522, the bumper 666 of the cornering arm 524 engages the corner 598 of the patch plate 160 and pushes the patch plate 160 toward the reference corner (570 in FIG. 14), e.g., the "A1" reference corner, positioned diagonally across from the bumper 666 of the cornering arm 524. As the bumper 666 pushes the patch plate 160 into the reference corner 570, the patch plate 160 engages the bosses (642, 644, 646, 648, 650, 652, and 654 in FIG. 14) at the edges (620, 622, 624, and 626 in FIG. 14) of the turntable body 522, which restrain further movement of the patch plate 160. Accordingly, any offset errors accumulated during handling of the patch plate 160 may be corrected when the bumper 666 of the cornering arm 524 pushes the patch plate 160 into the reference corner 570 and against the bosses 642, 644, 646, 648, 650, 652, and 654.

The turntable body 522 also includes a recess (619 in FIG. 14) that houses a spring (526 in FIG. 14), which biases the cam-engagement end 662 of the cornering arm 524 away from the turntable body 522. The spring 526, in this example, engages a triangular projection 668 formed on the cam-engagement end 662 of the cornering arm 524 such that the cam-engagement end 662 pivots about the pivot pin 658 away from the turntable body 522. Therefore, when the cam-engagement end 662 pivots away from the turntable body 522, the plate-engagement end 664 pivots toward the turntable body 522. Adjusting the position of a patch plate 160 resting on the turntable 50 will be discussed in further detail below with reference to FIG. 16 and FIGS. 17A-D.

Figure 16:
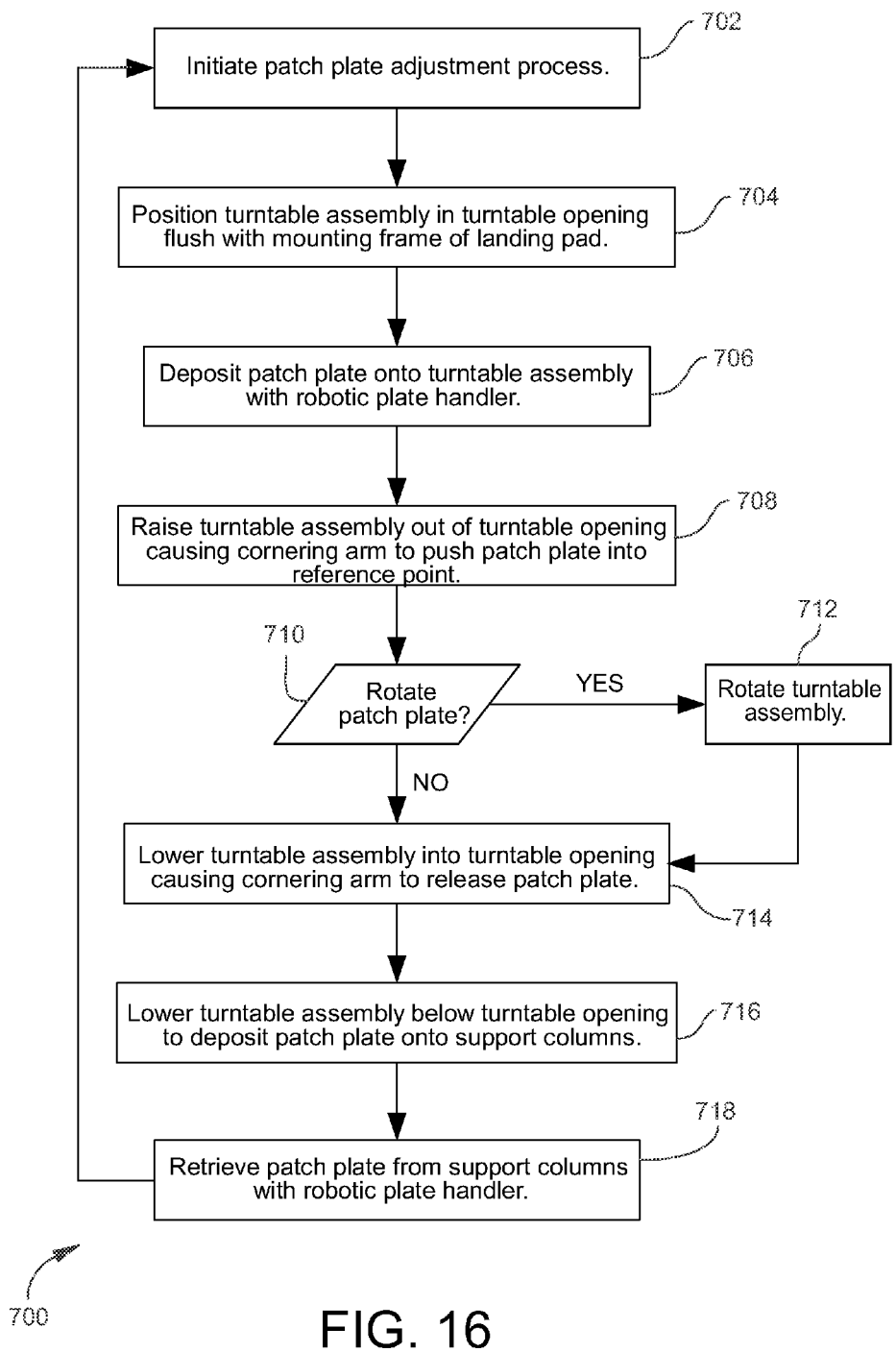
FIG. 16 is a flowchart of example method steps for adjusting a patch plate in order to correct offset errors accumulated during handling of the patch plate.

Referring now to FIG. 16, a flowchart 700 of example method steps for adjusting a patch plate (160 in FIG. 12) in order to correct offset errors accumulated during handling of the patch plate 160 is shown. FIG. 16 will be discussed in conjunction with FIGS. 17A-D, which illustrate the stages of operation of the automated reorientation apparatus (500 in FIG. 12) during the patch plate adjustment process.

When the patch plate adjustment process is initiated (step 702), the turntable (510 in FIG. 12) may be positioned in the turntable opening (516 in FIG. 12) of the mounting frame (508 in FIG. 12) (step 704). The turntable 510 may be positioned within the turntable opening (516 in FIG. 12) of the mounting frame 508 such that the top side of the turntable 510 is flush with the top side of the mounting frame 508. Positioning the turntable 510 in the turntable opening 516 may involve lowering the turntable 510 if the turntable 510 is in a raised position or raising the turntable 510 if the turntable 510 is in a lowered position.

Figure 17A:
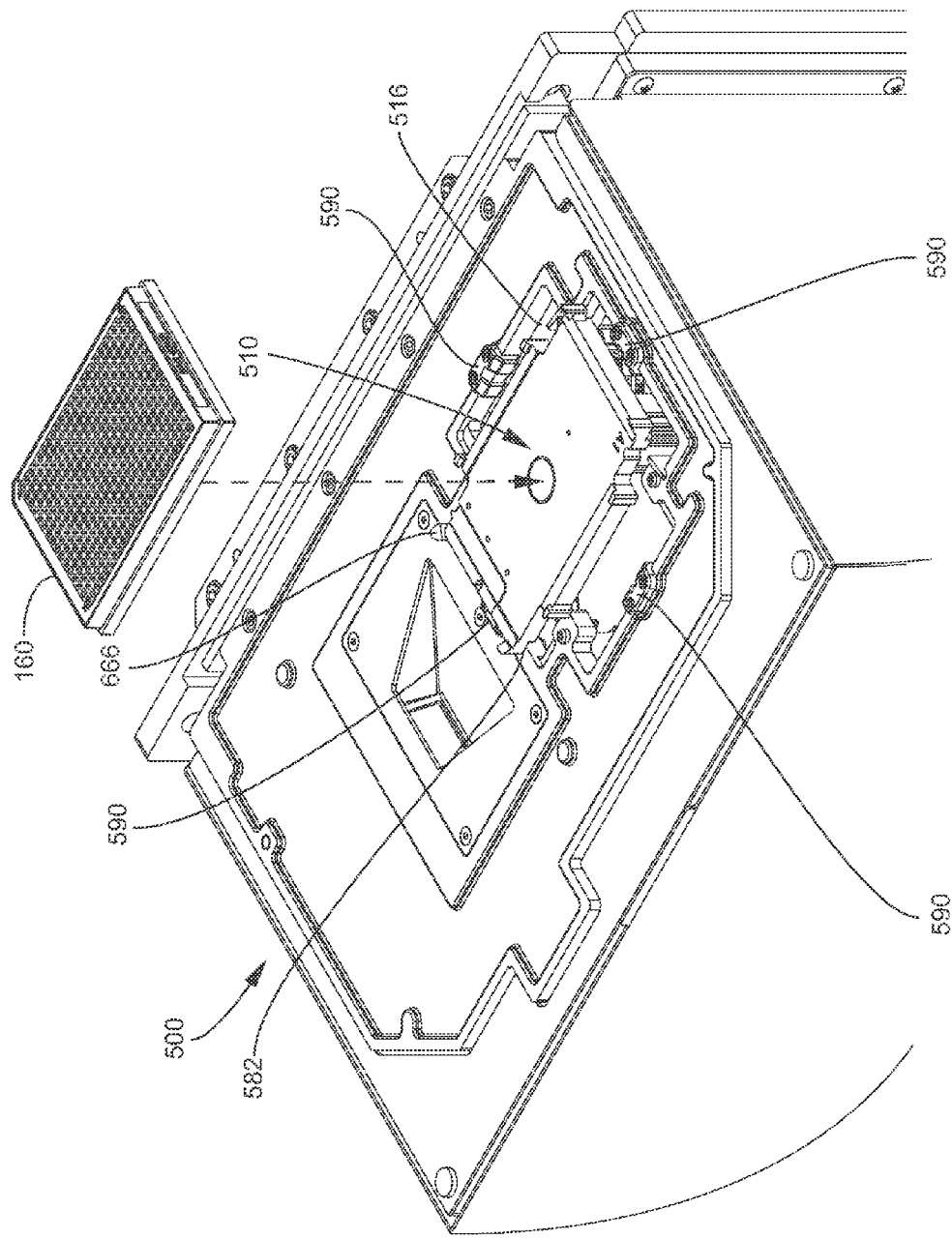
FIG. 17A is a front top-left perspective view of an example of an implementation of an automated reorienting apparatus in a first stage of operation.

In FIG. 17A, an example of an automated reorientation apparatus 500 is shown with the turntable 510 positioned in the turntable opening 516 at the start of a patch plate readjustment process. When the turntable 510 is raised or lowered into the turntable opening 516, the cam follower (660 in FIG. 15) of the cornering arm (524 in FIG. 12) engages one of the cornering cams 590 of the turntable opening 516. In the example shown in FIG. 17A, the cam follower 660 engages the cornering cam 590 at the top interior edge 582 of the turntable opening 516. As the turntable 510 continues to move through the turntable opening 516, the cornering cam 590 pushes the cam follower 660 toward the turntable 510 thereby loading the spring (526 in FIG. 14) in the turntable 510. While the turntable 510 resides within the turntable opening 516, the cornering cam 590 prevents the spring 526 from unloading and pushing the cam follower 660 outward and away from the turntable 510. In other words, the spring 526 housed within the turntable 510 is continually loaded while the turntable 510 resides within the turntable opening 516 since the cornering cam 590 blocks the outward movement of the cam follower 660. Accordingly, as set forth above, when the cam follower 660 of the cornering arm 524 pivots toward the turntable 510, the bumper 666 of the cornering arm 524 pivots away from the turntable 510. In FIG. 17A, the turntable 510 is positioned within the turntable opening 516, and thus the bumper 666 of the cornering arm 524 is positioned away from the turntable 510.

Figure 17B:
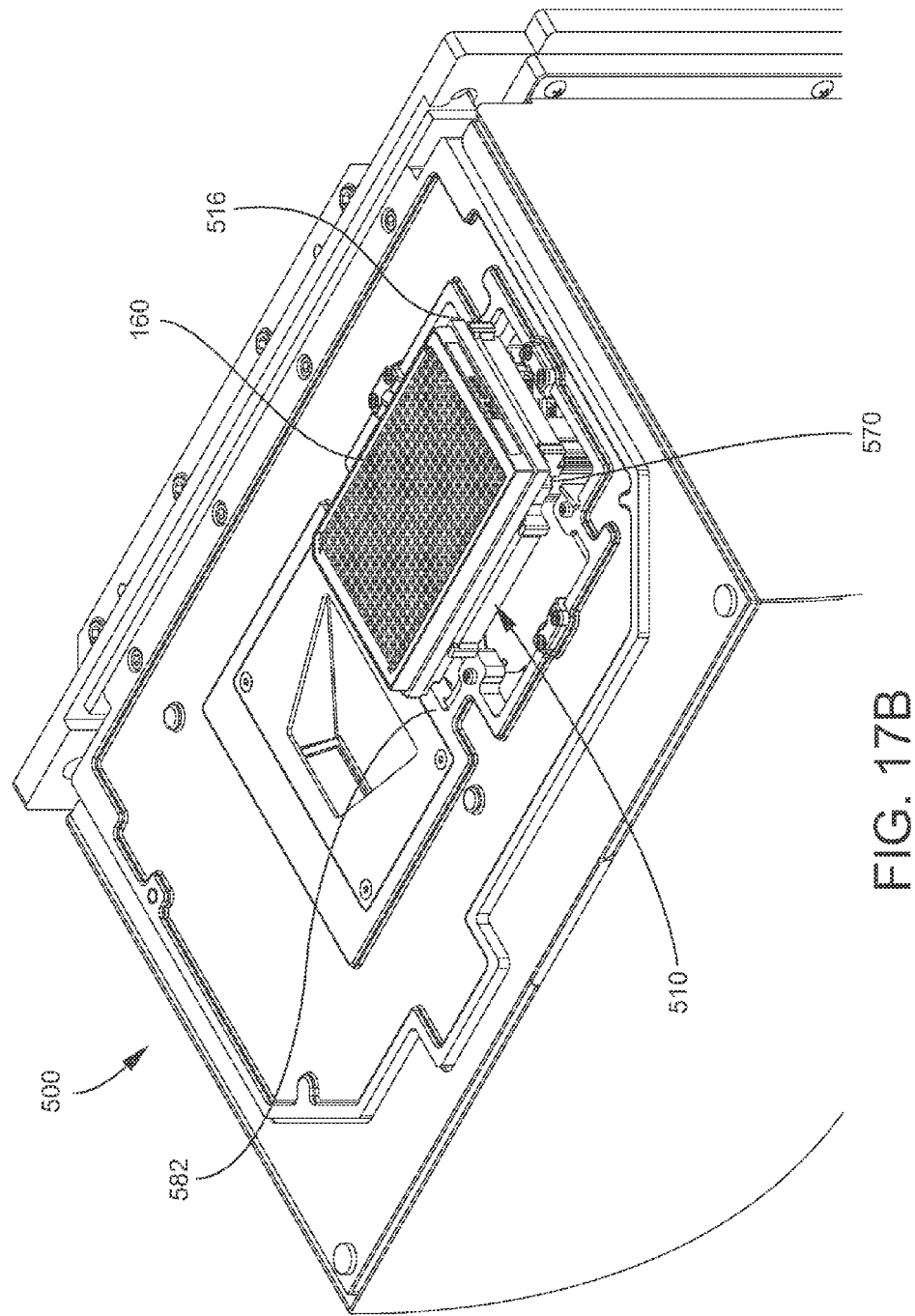
FIG. 17B is a front top-left perspective view of the automated orientation apparatus of FIG. 17A in a second stage of operation.

Referring back to FIG. 16, the robotic plate handler deposits the patch plate 160 (or other similarly-sized component) onto the turntable 510 (step 706) residing in the turntable opening 516. Alternatively, the patch plate 160 may be manually placed on the turntable 510. In FIG. 17B, the automated reorientation apparatus 500 of FIG. 17A is shown with the turntable 510 supporting a patch plate 160 that has been deposited onto the turntable 510.

With the turntable 510 supporting the patch plate 160, the elevating arm (514 in FIG. 12) may raise the turntable 510 out of the turntable opening 516 (step 708), which causes the cornering arm 524 to push the patch plate 160 resting on the turntable 510 toward the reference corner (570 in FIG. 12) on the turntable 510. As set forth above, the spring (526 in FIG. 14) in the turntable 510 biases the cam follower 660 of the cornering arm 524 away from the turntable 510, and the cornering cam 590 on the interior edge 582 of the turntable opening 516 keeps the spring 526 loaded while the turntable 510 resides in the turntable opening 516.

The cornering cam 590 includes, however, a beveled edge (592 in FIG. 12), e.g., a 45° beveled edge 592, as also explained above. As the turntable 510 rises upward past the beveled edge 592, the spring 526 gradually unloads to push the cam follower 660 away from the turntable 510 and up the beveled edge 592 of the cam follower 660. As the spring 526 pushes the cam follower 660 away from the turntable 510, the cornering arm 524 pivots about the pivot pin (658 in FIG. 15). Accordingly, the bumper 666 on the plate-engagement end (664 in FIG. 15) of the cornering arm 524 pivots toward the patch plate 160. As the turntable 510 rises past the beveled edge 592, the bumper 666 of the cornering arm 524 will thus gradually push the patch plate 160 resting on the turntable 510 toward the reference corner 570 thereby correcting any accumulated offset errors.

Figure 17C:
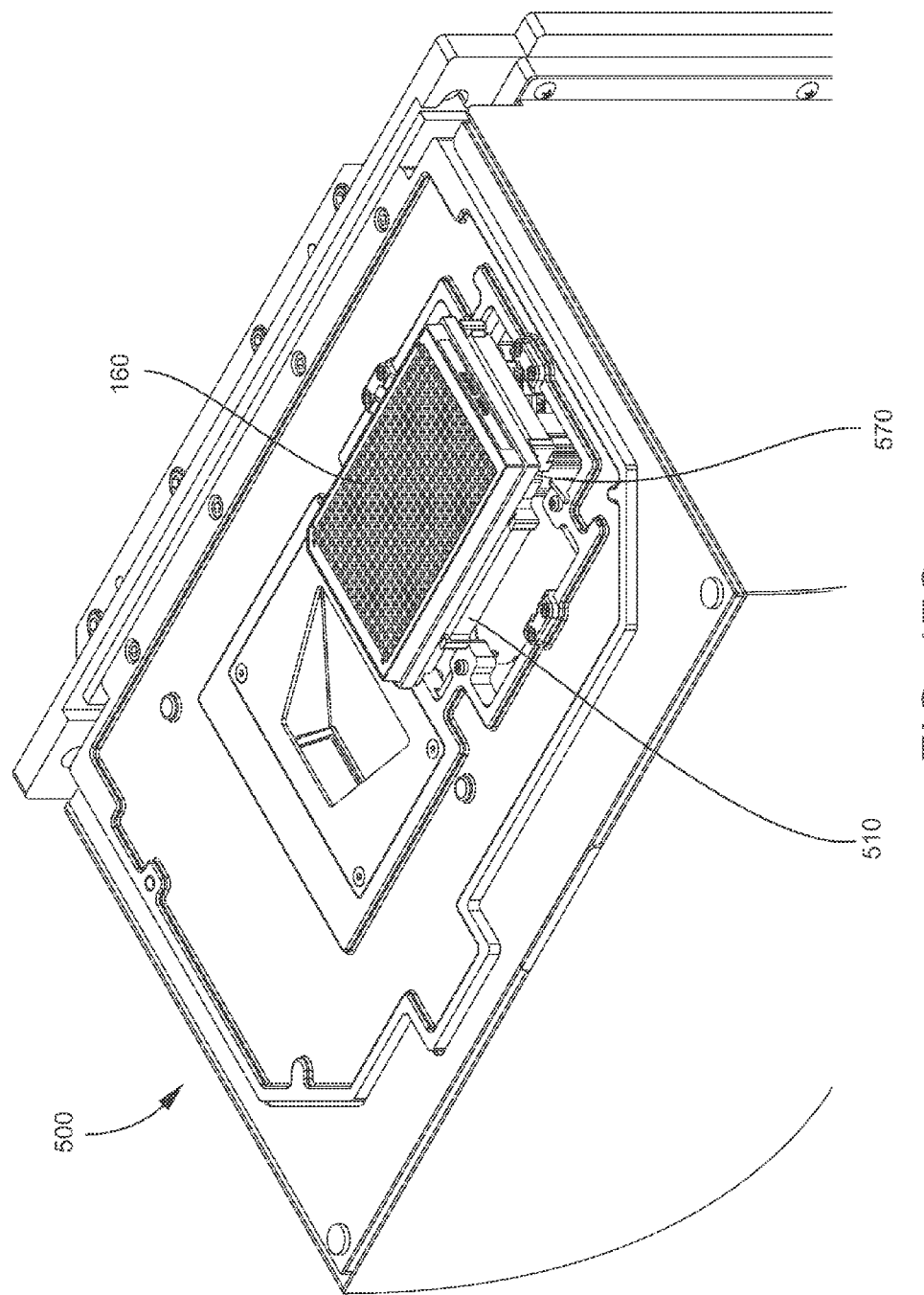
FIG. 17C is a front top-left perspective view of the automated orientation apparatus of FIG. 17A in a third stage of operation.

In FIG. 17C, the automated reorientation apparatus 500 of FIG. 17B is shown with the turntable 510 in a raised position having used the cornering arm (524 in FIG. 14) to push the patch plate 160 into the reference corner 570. As seen in FIG. 17C, the bumper 666 of the cornering arm 524 has pivoted towards the turntable 510 due to the spring (526 in FIG. 14) biasing the cam follower (660 in FIG. 15) away from the turntable 510. While the turntable 510 is in the raised position, the turntable 510 may rotate the patch plate 160 in order to change the orientation (e.g., 0°, 90°, 180°, or 270°) of the patch plate 160 if desired or needed.

Referring back to FIG. 16, if the patch plate 160 should be reoriented (step 710), the rotary actuator (520 in FIG. 12) may drive rotation of the turntable 510 in order to rotate the patch plate 160 resting on the turntable 510 (step 712). The patch plate 160 may, for example, be rotated in order to bring a barcode on one side of the patch plate 160 within view of a barcode reader (610 in FIG. 12) at the landing pad (502 in FIG. 11) as mentioned above. The patch plate 160 may also be rotated in order to align the patch plate 160 with a component of the automated, high-throughput electrophysiology measurement system (100 in FIG. 1).

If the patch plate 160 does not need to be rotated (step 710), or after rotation of the patch plate 160, the elevating arm (514 in FIG. 12) may lower the turntable 510 back into the turntable opening 516 (step 714) to cause the cornering arm 524 to release the patch plate 160 resting on the turntable 510. As the turntable 510 lowers into the turntable opening 516, the cam follower 660 again engages the beveled edge 592 of the cornering cam 590. As the turntable 510 lowers past the cam follower 660, the beveled edge 592 gradually pushes the cam follower 660 toward the turntable 510 thereby gradually loading the spring 526 housed within the turntable 510. As the beveled edge 592 pushes the cam follower 660 towards the turntable 510, the cornering arm 524 pivots about the pivot pin 658. Accordingly, the bumper 666 on the plate-engagement end 664 of the cornering arm 524 pivots away from the turntable 510 and patch plate 160 thereby releasing the patch plate 160.

The elevating arm 514 may continue to lower the turntable 510 below the turntable opening 516 (step 716) in order to deposit the adjusted patch plate 160 on the support columns (596 in FIG. 12) at the turntable opening 516. As explained above, the corners (598 in FIG. 12) of the patch plate 160 hang over the exterior corners (632, 634, 636, and 638 in FIG. 14) of the turntable body 522. The support columns 596 at the turntable opening 516 are received in these exterior corners 632, 634, 636, and 638 as the turntable 510 moves through the turntable opening 516. Accordingly, the support columns 596 engage the underside of the patch plate 160 at the overhanging patch plate corners 598 as the turntable 510 continues to lower through the turntable opening 516.

Figure 17D:
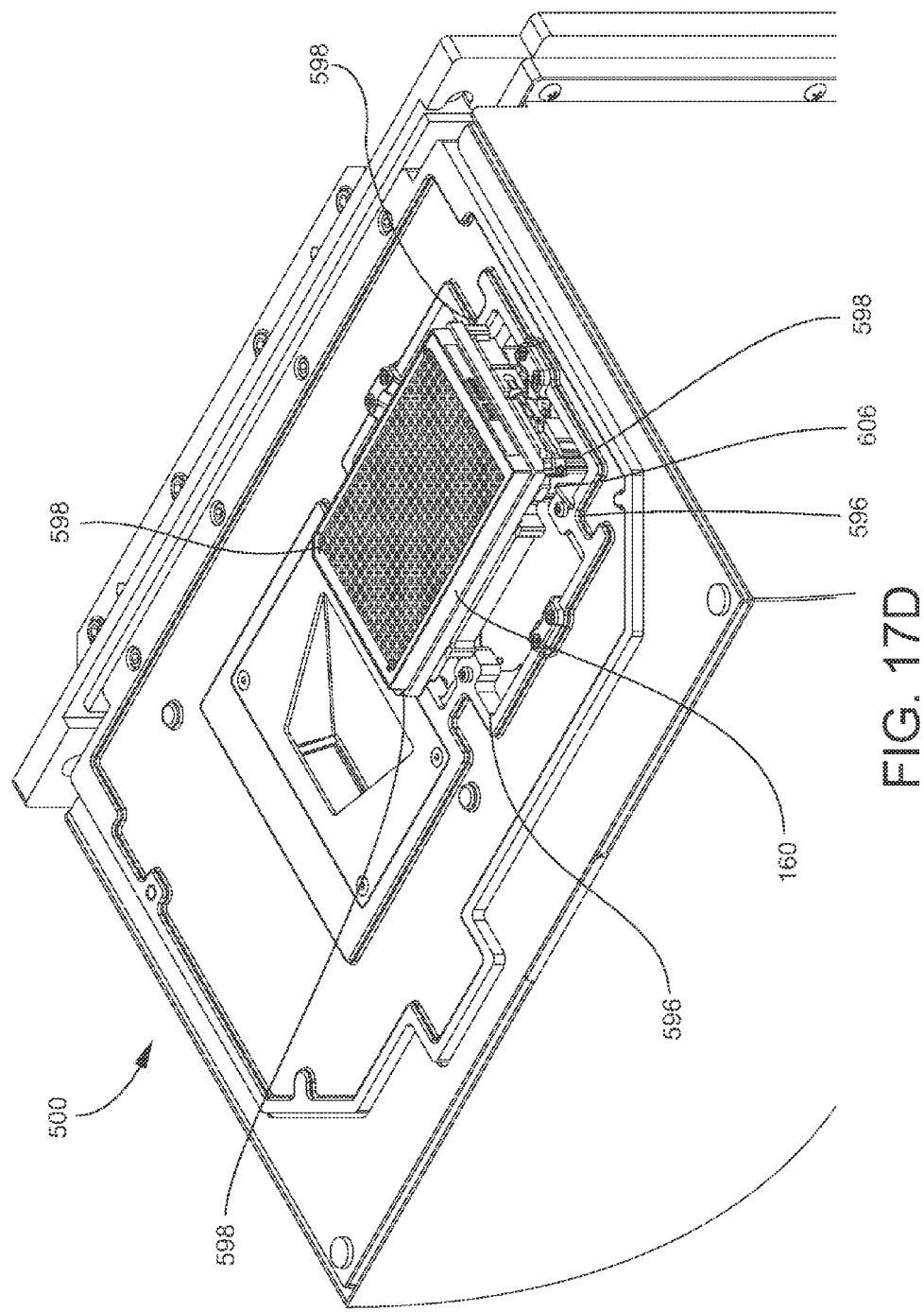
FIG. 17D is a front top-left perspective view of the automated orientation apparatus of FIG. 17A in a fourth stage of operation.

In this way, the adjusted patch plate 160 may be deposited at the support columns 596 after the cornering arm 524 adjusts the position of the patch plate 160 or after the patch plate 160 is rotated to a new orientation. In FIG. 17D, the automated reorientation apparatus 500 of FIG. 17C is shown having deposited the adjusted patch plate 160 onto the support columns 596 at the turntable opening 516. The elevating arm (514 in FIG. 12) has lowered the turntable (510 in FIG. 12) below the turntable opening 516, and the corners 598 of the patch plate 160 are supported by the support columns 596. Also seen in FIG. 17D, the adjusted patch plate 160 is engaging the tab 606 of the patch plate detection assembly (602 in FIG. 12) positioned next to the bottom-left support column 596. A control module (104 in FIG. 1) connected to the patch plate detection assembly 602 may determine that the patch plate 160 is in a portrait orientation as shown by way of example in FIG. 17D.

Referring back to FIG. 16, having deposited the adjusted patch plate 160 on the support columns 596, the robotic plate handler may retrieve the adjusted patch plate 160 from the support columns 596 (step 718). Accumulated offset errors may be corrected at periodic intervals by repeating steps 702-718.

In general, terms such as "communicate" and "in . . . communication with" (for example, a first component "communicates with" or "is in communication with" a second component) are used herein to indicate a structural, functional, mechanical, electrical, signal, optical, magnetic, electromagnetic, ionic or fluidic relationship between two or more components or elements. As such, the fact that one component is said to communicate with a second component is not intended to exclude the possibility that additional components may be present between, and/or operatively associated or engaged with, the first and second components.

The foregoing description of implementations has been presented for purposes of illustration and description. It is not exhaustive and does not limit the claimed inventions to the precise form disclosed. Modifications and variations are possible in light of the above description or may be acquired from practicing the invention. The claims and their equivalents define the scope of the invention.

What is claimed is:

1. An apparatus for automatically conditioning a patch plate and a plenum of an electrophysiology measurement system comprising:
   an arm having an operative end and linearly movable into a space between the patch plate and the plenum at an operative position and linearly movable out of the space at a non-operative position ;
   a first end effector mounted to a first side of the operative end of the arm facing the patch plate and configured to condition the patch plate;
   a second end effector mounted to a second side of the operative end of the arm opposite the first side facing the plenum and configured to condition the plenum; and
   a linear actuator coupled to the arm wherein the linear actuator is configured to drive movement of the arm between the operative position and the non-operative position such that, when the arm is positioned at the operative position, the arm is situated between the patch plate and the plenum.

2. The apparatus of claim 1 wherein:
   the first end effector is an upward-facing end effector mounted to a top side of the arm and configured to condition a bottom surface of the patch plate; and
   the second end effector is a downward-facing end effector mounted to a bottom side of the arm and configured to condition a top surface of the plenum.

3. The apparatus of claim 2 wherein the upward-facing end effector comprises a first vacuum nozzle configured to aspirate residual fluid from the bottom surface of the patch plate and the downward-facing end effector comprises a second vacuum nozzle configured to aspirate residual fluid from the top surface of the plenum and further comprising:
   a collection receptacle communicating with the first vacuum nozzle and the second vacuum nozzle via respective conduit lines; and
   a vacuum pump communicating with the collection receptacle and configured to create a vacuum such that the residual fluid is drawn into the collection receptacle via the conduit lines.

4. The apparatus of claim 1 wherein the second end effector comprises an atmospheric-pressure plasma head configured to dispense plasma on the plenum and further comprising:
   a plasma gas source communicating with the atmospheric-pressure plasma head and configured to provide gas to the atmospheric-pressure plasma head; and
   a power source communicating with the atmospheric-pressure plasma head and configured to apply a voltage potential sufficient to produce the plasma from the gas received at the atmospheric-pressure plasma head.

5. The apparatus of claim 1 wherein the second end effector comprises an electrode conditioner configured to remove chloride from one or more electrodes residing at the plenum and further comprising:
   a cathode configured to be submerged in an electrically conductive solution contained in the plenum; and
   a power source configured to apply a voltage potential between the cathode and the one or more electrodes residing at the plenum, wherein the voltage potential is sufficient to cause migration of chloride toward the cathode.

6. The apparatus of claim 1, wherein the first end effector comprises a first vacuum nozzle, and the second end effector comprises a component selected from the group consisting of: a second vacuum nozzle, an atmospheric-pressure plasma head, an electrode conditioner, and a combination of two or more of the foregoing.

* * * * *